US006861439B2

(12) United States Patent
Haque et al.

(10) Patent No.: US 6,861,439 B2
(45) Date of Patent: Mar. 1, 2005

(54) TREATMENT OF CEREBROVASCULAR DISEASE

(75) Inventors: Wasimul Haque, Edmonton (CA); Rajat Sethi, Winnipeg (CA)

(73) Assignee: Medicure International, Inc., Barbados (BB)

( * ) Notice: Subject to any disclaimer, the term of this patent is extended or adjusted under 35 U.S.C. 154(b) by 0 days.

(21) Appl. No.: 10/254,197

(22) Filed: Sep. 24, 2002

(65) Prior Publication Data

US 2003/0114424 A1 Jun. 19, 2003

Related U.S. Application Data

(62) Division of application No. 09/820,199, filed on Mar. 28, 2001, now Pat. No. 6,586,414.
(60) Provisional application No. 60/192,774, filed on Mar. 28, 2000.

(51) Int. Cl.$^7$ .......................................... A61K 31/4355
(52) U.S. Cl. .................... 514/302; 514/321; 514/233.5; 514/253.04
(58) Field of Search ............................ 514/302, 233.5, 514/253.04, 321, 233.8

(56) References Cited

U.S. PATENT DOCUMENTS

| | | | |
|---|---|---|---|
| 3,206,463 A | 9/1965 | Baetz | 260/295 |
| 3,910,921 A | 10/1975 | Esanu | 260/286 R |
| 3,987,177 A | 10/1976 | Giudicelli et al. | 424/267 |
| 4,032,534 A | 6/1977 | Chodkiewicz | 260/306.7 C |
| 4,036,844 A | 7/1977 | Thorne et al. | 260/295 R |
| 4,053,607 A | 10/1977 | Thorne et al. | 424/263 |
| 4,137,316 A | 1/1979 | Esanu | 424/256 |
| 4,167,562 A | 9/1979 | Evers | 424/153 |
| 4,361,570 A | 11/1982 | Fici | 424/263 |
| 4,369,172 A | 1/1983 | Schor et al. | 424/19 |
| 4,374,841 A | 2/1983 | Descamps et al. | 424/263 |
| 4,515,771 A | 5/1985 | Fine | 424/52 |
| 4,567,179 A | 1/1986 | Lombardino | 514/225 |
| 4,569,938 A | 2/1986 | Esanu | 514/302 |
| 4,569,939 A | 2/1986 | Esanu | 514/302 |
| 4,581,363 A | 4/1986 | Esanu | 514/302 |
| 4,605,741 A | 8/1986 | Zagnoli et al. | 546/24 |
| 4,730,042 A | 3/1988 | Hege et al. | 544/124 |
| 4,735,950 A | 4/1988 | Esanu | 514/302 |
| 4,735,956 A | 4/1988 | Baldwin et al. | 514/338 |
| 4,837,239 A | 6/1989 | Benjamin et al. | 514/267 |
| 4,843,071 A | 6/1989 | Hohenwarter | 514/217 |
| 4,962,121 A | 10/1990 | Hamberger et al. | 514/419 |
| 5,001,115 A | 3/1991 | Sloan | 514/34 |
| 5,053,396 A | 10/1991 | Blass | 514/45 |
| 5,118,505 A | 6/1992 | Koltringer | 424/195.1 |
| 5,130,324 A | 7/1992 | Ulrich et al. | 514/357 |
| 5,132,115 A | 7/1992 | Wolter et al. | 424/448 |
| 5,210,083 A | 5/1993 | Pfirrmann | 514/222.5 |
| 5,213,813 A | 5/1993 | Kornecki et al. | 424/532 |
| 5,254,557 A | 10/1993 | Buckle et al. | 514/269 |
| 5,254,572 A | 10/1993 | Serfontein | 514/345 |
| 5,272,165 A | 12/1993 | Ulrich et al. | 514/357 |
| 5,278,154 A | 1/1994 | Lacoste et al. | 514/114 |
| 5,288,716 A | 2/1994 | Speck | 514/89 |
| 5,326,757 A | 7/1994 | Demopoulos | 514/167 |
| 5,328,453 A | 7/1994 | Sibalis | 604/20 |
| 5,372,999 A | 12/1994 | Schneider et al. | 514/81 |
| 5,385,937 A | 1/1995 | Stamler et al. | 514/557 |
| 5,420,112 A | 5/1995 | Lewis et al. | 514/12 |
| 5,441,972 A | 8/1995 | Ogata et al. | 514/342 |
| 5,504,090 A | 4/1996 | Neely | 514/263 |
| 5,563,126 A | 10/1996 | Allen et al. | 514/52 |
| 5,569,459 A | 10/1996 | Shlyankevich | 424/195.1 |
| 5,569,648 A | 10/1996 | Lewis et al. | 514/12 |
| 5,631,271 A | 5/1997 | Serfontein | 514/345 |
| 5,633,228 A | 5/1997 | Lewis et al. | 514/12 |
| 5,648,335 A | 7/1997 | Lewis et al. | 514/12 |
| 5,728,684 A | 3/1998 | Cheng et al. | 514/50 |
| 5,733,884 A | 3/1998 | Barbul et al. | 514/21 |
| 5,733,916 A | 3/1998 | Neely | 514/262 |
| 5,770,215 A | 6/1998 | Moshyedi | 424/440 |
| 5,795,873 A | 8/1998 | Allen | 514/52 |
| 5,804,163 A | 9/1998 | Gibby et al. | 424/9.361 |
| 5,804,594 A | 9/1998 | Murad | 514/474 |
| 5,833,998 A | 11/1998 | Biedermann et al. | 424/401 |
| 5,834,446 A | 11/1998 | Dow et al. | 514/58 |
| 5,840,685 A | 11/1998 | Fujii et al. | 514/12 |
| 5,847,008 A | 12/1998 | Doebber et al. | 514/708 |
| 5,858,017 A | 1/1999 | Demopulos et al. | 604/890.1 |
| 5,859,051 A | 1/1999 | Adams et al. | 514/469 |
| 5,874,420 A | 2/1999 | Pelleg | 514/81 |
| 5,874,443 A | 2/1999 | Kiely et al. | 514/309 |
| 5,888,514 A | 3/1999 | Weisman | 424/195.1 |
| 5,944,020 A | 8/1999 | Markov et al. | 128/898 |
| 6,043,259 A | 3/2000 | Dhalla et al. | 514/345 |
| 6,310,093 B1 | 10/2001 | Newcomb | 514/496 |
| 6,339,085 B1 * | 1/2002 | Haque | 514/233.8 |

FOREIGN PATENT DOCUMENTS

| | | |
|---|---|---|
| BE | 831350 | 1/1976 |
| BE | 863754 | 5/1978 |
| CH | 561 183 | 4/1975 |

(List continued on next page.)

OTHER PUBLICATIONS

Aybak, M. et al., "Effect of Oral Pyridoxine Hydrochloride Supplementation on Arterial Blood Pressure in Patients with Essential Hypertension", *Drug Res.*, vol. 45, No. 12, pp. 1271–1273 (1995).

"B Vitamins May Cut Heart Disease Risk", *Harvard Health Letter*, 1 page (1998).

Baliga, B. et al., "Hyperhomocysteinemia in Type 2 Diabetes Mellitus: Cardiovascular Risk Factors and Effect of Treatment with Folic Acid and Pyridoxine", *Endocrine Practice*, vol. 6, No. 6, pp. 435–441 (Nov./Dec. 2000).

(List continued on next page.)

*Primary Examiner*—Phyllis Spivack
(74) *Attorney, Agent, or Firm*—Merchant & Gould

(57) ABSTRACT

A method of treating a cerebrovascular disease, particularly stroke, is described. A method of treating a cerebrovascular disease includes administering pyridoxal-5'-phosphate, pyridoxal, pyridoxine, pyridoxamine, 3-acylated analogues of pyridoxal, 3-acylated analogues of pyridoxal-4,5-aminal, pyridoxine phosphonate analogues, or pharmaceutical compositions thereof.

17 Claims, 4 Drawing Sheets

FOREIGN PATENT DOCUMENTS

| | | |
|---|---|---|
| DE | 1 958 226 | 5/1970 |
| DE | 24 61 742 A | 7/1976 |
| DE | 37 05 549 A1 | 9/1988 |
| DE | 43 44 751 A1 | 6/1995 |
| EP | 0 121 036 A1 | 10/1984 |
| EP | 0 144 051 A2 | 6/1985 |
| EP | 0 270 026 A2 | 6/1988 |
| EP | 0 416 248 A2 | 3/1991 |
| EP | 0 891 719 A1 | 1/1999 |
| FR | 846376 | 3/1941 |
| FR | 1323941 | 12/1963 |
| FR | 5552 M | 12/1967 |
| FR | 6453 M | 12/1968 |
| FR | 1579544 | 8/1969 |
| FR | 2034 539 | 12/1970 |
| FR | 2101010 | 3/1972 |
| FR | 2255883 | 7/1975 |
| FR | 2428640 | 1/1980 |
| GB | 1 013 939 | 12/1965 |
| GB | 1172800 | 12/1969 |
| GB | 1 201 014 | 8/1970 |
| GB | 1 297 080 | 11/1972 |
| GB | 1 360 536 | 7/1974 |
| GB | 1 493 993 | 12/1977 |
| GB | 2 254 556 A | 10/1992 |
| WO | WO 83/00085 | 1/1983 |
| WO | WO 91/19500 | 12/1991 |
| WO | WO 94/18965 | 9/1994 |
| WO | WO 98/19690 | 5/1998 |
| WO | WO 99/003365 | 1/1999 |
| WO | WO 99/53928 | 10/1999 |

OTHER PUBLICATIONS

Barrett, S., "Homocysteine: A Cardiovascular Risk Factor Worth Considering", http://www.quackwatch.com/03HealthPromotion/homocysteine.html, 2 pages (©1997).

Bernstein, A., "Vitamin $B_6$ in Clinical Neurology", Annals of New York Academy of Sciences, vol. 585, pp. 250–260 (1990).

Berger, A.R. et al., "Dose response, coasting, and differential fiber vulnerability in human toxic neuropathy: A prospective study of pyridoxine neurotoxicity", Neurology, vol. 42, No. 7, pp. 1367–1370 (Jul. 1992).

Bhagavan, H. et al., "Effect of Postweanling Pyridoxine Deficiency on Growth and Concentration of the Coenzyme Pyridoxal–5'–phosphate in Heart, Kidneys, Lungs, and Adrenals in Rats", Pediat. Res., vol. 10, pp. 730–732 (1976).

Bode, W. et al., "Pyridoxal–5'–Phosphate and Pyridoxal Biokinetics in Male Wistar Rats Fed Graded Levels of Vitamin B–6", Nutr., vol. 121, No. 11, pp. 1738–1745 (Nov. 1991).

Chasan–Taber, L. et al., "A Prospective Study of Folate and Vitamin $B_6$ and Risk of Myocardial Infarction in US Physicians", Journal of the American College of Nutrition, vol. 15, No. 2, pp. 136–143 (Apr. 1996).

Cho, Y. et al., "In Vivo Evidence for a Vitamin B–6 Requirement in Carnitine Synthesis", J. Nutr., vol. 120, pp. 258–265 (1990).

Ellis, J. et al., "Prevention of Myocardial Infarction by Vitamin $B_6$", Res. Commun. Molec. Pathol. Pharmacol., vol. 89, No. 2, pp. 208–220 (Aug. 1995).

Folsom, A. et al., "Clinical Investigation and Reports: Prospective Study of Coronary Heart Disease Incidence in Relation to Fasting Total Homocysteine, Related Genetic Polymorphisms, and B Vitamins: The Atherosclerosis Risk in Communities (ARIC) Study", Circulation, vol. 98, pp. 204–210 (Jul. 21, 1998).

Harada, K. et al., "Studies on Vitamin $B_{6-}$ (IV) Behavior of Pyridoxal Acylates in the Body After Parenteral Administration", Vitamins Journal of the Vitamin Society of Japan, vol. 45, No. 2, pp. 69–75 (Feb. 1972).

Hathcock, J., "Vitamins and minerals: efficacy and safety", Am J Clin Nutr, vol. 66, pp. 427 –437 (1997).

Hoover, D.M. et al., "Ultrastructural Lesions of Pyridoxine Toxicity in Beagle Dogs", Vet. Pathol., vol. 18, pp. 769–777 (1981).

Kok, F. et al., "Low Vitamin $B_6$ Status in Patients with Acute Myocardial Infarction", Am. J. Cardiol., vol. 63, pp. 513–516 (Mar. 1, 1989).

Korytnyk et al. Schiff Bases of Pyriodoxal: Their Structure and Stabilization of their Ring–Chain Tautomeric Forms by Acylation, Tetrahedron, 26 (23), 5415–25 (1982).

Krinke, G. et al., "Pyridoxine Megavitaminosis: An Analysis of the Early Changes Induced with Massive Doses of Vitamin $B_6$ in Rat Primary Sensory Neurons", J. Neuropathol. Exp. Neurol., vol. 44, No. 7, pp. 117–129 (Mar. 1985).

Kubyshkin, V. et al., "Comparative characteristics of the arrhythmic syndrome and the possibility for its coenzyme correlation in dilated and hypertrophic cardiomyopathy", Abstract, 1 pg. (1989).

Lal, K. et al., "Hypotensive action of 5–HT receptor agonists in the vitamin $B_6$–deficient hypertensive rat", Eur. J. Pharmacol., vol. 234, Nos. 2/3, pp. 183–189 (Apr. 1993).

Lal, K. et al., "Calcium channels in vitamin $B_6$ deficiency–induced hypertension", Journal of Hypertension, vol. 11, No. 12, pp. 1357–1362 (Dec. 1993).

Lal, K. et al., "The effect of vitamin $B_6$ on the systolic blood pressure of rats in various animal models of hypertension", Journal of Hypertension, vol. 14, No. 3, pp. 355–363 (Mar. 1996).

Levy, H. et al., "Pyridoxine Deficiency in Congestive Heart Failure", P.S.E.B.M., vol. 101, pp. 617–621 (1959).

Manore, M. et al., "Changes in Plasma Pyridoxal Phosphate (PLP) In Diabetic (D), Hypertensive (HTN) and Hypertensive–diabetic (HTN–D) Men Fed A Constant Vitamin B–6 (B6) Diet", Source Unknown, pp. 1254 (1990) (Abstract).

Markov, A. et al, "Hemodynamic, electrocardiographic, and metabolic effects of fructose diphosphate on acute myocardial ischemia", American Heart Journal, vol. 100, No. 5, pp. 639 –646 (Nov. 1980).

Mendelsohn, A. et al., "Hemodynamic and Clinical Effects of Oral Levodopa in Children With Congestive Heart Failure", JACC, vol. 30, No. 1, pp. 237–242 (Jul. 1997).

Merrill, Jr. et al. A. et al., "Diseases associated with defects in vitamin $B_6$ metabolism or utilization", Ann. Rev. Nutr., vol. 7, pp. 137–156 (1987).

Mulvaney, D. et al., "Electrocardiographic changes in vitamin $B_6$ deficient rats", Cardiovascular Research, vol. 13, pp. 506–513 (1979).

Omenn, G. et al., "Preventing Coronary Heart Disease", Circulation, vol. 97, pp. 421–424 (1998).

Paulose, C. et al., "Sympathetic Stimulation and Hypertension in the Pyridoxine–Deficient Adult Rat", Hypertension, vol. 11, No. 4, pp. 387–391 (Apr. 1988).

Rao, R. et al., "Failure of Pyridoxine to Improve Glucose Tolerance in Diabetics", *Journal of Clinical Endocrinology & Metabolism,* vol. 50, No. 1, pp. 198–200 (Jan. 1980).

Rimm, E. et al., "Folate and Vitamin $B_6$ From Diet and Supplements in Relation to Risk of Coronary Heart Disease Among Women", *JAMA,* vol. 279, No. 5, pp. 359–364 (Feb. 4, 1998).

Sakuragi, T. et al., "The Synthesis of Long Chain Fatty Acid Derivatives of the Vitamin $B_6$ Group", *J. Am. Chem. Soc.,* vol. 78, pp. 839–842 (Feb. 20, 1956).

Sethi, R. et al., "Differential changes in left and right ventricular adenylyl cyclase activities in congestive heart failure", *The American Physiological Society,* vol. 272; No. 2, Part 2 of Two Parts, pp. H884 –H893 (Feb. 1997).

Sethi, R. et al., "Inotropic Responses to Isoproterenol in Congestive Heart Failure Subsequent to Myocardial Infarction in Rats", *Journal of Cardiac Failure,* vol. 1, No. 5, pp. 391 –399 (Dec. 1995).

Takuma, Y. et al., "Combination Therapy of Infantile Spasms With High–Dose Pyridoxal Phosphate and Low–Dose Corticotropin", *Journal of Child Neurology,* vol. 11, No. 1, pp. 35–40 (Jan. 1996).

Tanaka, T. et al., "Pyridoxine Derivatives", *Chemical Abstracts,* vol. 62, No. 12, 1 page (Jun. 7, 1965).

Trezise, D. et al., "$P_2$ purinoceptor antagonist properties of pyridoxal–5–phosphate", *Eur. J. Pharmacol.,* vol. 259, No. 3, pp. 295–300 (Jul. 11, 1994).

Vanderjagt, D. et al., "Vitamin $B_6$ Status in a Healthy Elderly Population", *Annals New York Academy of Sciences,* pp. 562–564 (1990).

Verhoef, P. et al., "A Common Mutation in the Methylene-tetrahydrofolate Reductase Gene and Risk of Coronay Heart Disease: Results Among U.S. Men", *JACC,* Vo. 32, No. 2, pp. 353 –359 (Aug. 1998).

Verhoef, P. et al., "Homocysteine Metabolism and Risk of Myocardial Infarction: Relation with Vitamins $B_6$, $B_{12}$, and Folate", *Am. J. Epidemiol.,* vol. 143, No. 9, pp. 845–859 (May 1, 1996).

Vermaak, W.J.H. et al., "Vitamin $B_6$ and coronary artery disease. Epidemiological observations and case studies", *Atherosclerosis,* vol. 63, pp. 235–238 (Feb. 1987).

Vidrio, H., "Interaction with Pyridoxal as a Possible Mechanism of Hydralazine Hypotension", *Journal of Cardiovascular Pharmacology,* vol. 15, pp. 150–156 (1990).

Viscontini, V. et al., "Über einige Derivate des Pyridoxals", *Helvetica Chimica Acta,* vol. 34, No. 296, pp. 2438–2439 (1951).

Volpe,J.J., "Management of Neonatal Seizures", *Critical Care Medicine,* vol. 5, No. 1, pp. 43–49 (Jan.–Feb. 1977).

Windebank, A., "Neurotoxicity of Pyridoxine Analogs Is Related to Coenzyme Structure", *Neurochemical Pathology,* vol. 3, pp. 159–167 (1985).

Yarat, A. et al., "Effect of vitamin B6 on lenses of diabetic rats", *Indian Journal of Experimental Biology,* vol. 36, pp. 1269–1272 (Dec. 1998).

Zempleni, J. et al., "The utilization of intravenously infused pyridoxine in humans", *Clinica Chimica Acta,* vol. 229, Nos. 1, 2, pp. 27–36 (Sep. 1994).

* cited by examiner

TREATMENT OF CEREBROVASCULAR DISEASE

This application is a divisional of application Ser. No. 09/820,199, filed Mar. 28, 2001, U.S. Pat. No. 6,586,414 which application are incorporated herein by reference.

PRIORITY OF INVENTION

This application claims priority of invention under 35 U.S.C. §119(e) from U.S. provisional application number 60/192,774, Mar. 28, 2000.

FIELD OF THE INVENTION

This invention relates to a method of treating a cerebrovascular disease, including stroke. A method of treating a cerebrovascular disease includes administering pyridoxal-5'-phosphate, pyridoxal, pyridoxine, pyridoxamine, 3-acylated analogues of pyridoxal, 3-acylated analogues of pyridoxal-4,5-aminal, pyridoxine phosphonate analogues, or a pharmaceutical composition thereof.

BACKGROUND

Cerebrovascular disease includes any abnormality of the brain resulting from a pathologic process of a blood vessel. A pathologic process of a blood vessel includes any one or more of the following: an occlusion of a blood vessel lumen by thrombus or embolus, a rupture of a blood vessel, an altered permeability of a blood-vessel wall, and increased viscosity or other change in the quality of blood.

Cerebrovascular disease is typically readily diagnosable because of how it manifests. Cerebrovascular disease typically manifests as a stroke. A stroke can be characterized as a sudden nonconvulsive, focal neurologic deficit. That is, stroke can be characterized as the death of brain tissue that results from lack of blood flow and insufficient oxygen to the brain. After heart disease and cancer, stroke is the leading cause of death in the United States. In the United States, there are approximately 500,000 cases of stroke annually. And these 500,000 cases give rise to about 175,000 fatalities.

A stroke can be ischemic or hemorrhagic. In an ischemic stroke, the blood supply to part of the brain is reduced or terminated either by a blood clot that blocks a blood vessel or by atherosclerosis. Reducing or terminating blood flow to the brain is known as cerebral ischemia. Cerebral ischemia can last for seconds to minutes, and when cerebral ischemia occurs for more than a few minutes, infarction of brain tissue results. A blood vessel can be blocked by a blood clot that arises from thrombus or embolus. Yet cerebral ischemia can also arise from the failure of circulation and hypotension from severe and prolonged cardiac decompensation or shock.

In a hemorrhagic stroke, the brain is damaged by a blood vessel bursting, which prevents normal blood flow and allows blood to leak into an area of the brain. In some instances, the blood leaks from a small artery. When blood leaks into the brain, a hematoma is formed in the brain and blood can spread into ventricles and subarachnoid space.

In cerebral hemorrhage, blood leaks from the vessel (usually a small artery) directly into the brain forming a hematoma, and the blood spreads into the ventricles and subarachnoid space. The hematoma can cause physical disruption of the brain tissue and pressure on the surrounding brain areas. When the blood leakage stops, the hematoma can slowly disintegrate and be absorbed over a period of weeks and months.

Several factors, including hypertension, heart disease, atrial fibrillation, diabetes mellitus, cigarette smoking of long duration, hyperlipidemia, use of birth control pills, and systemic diseases associated with a hypercoagulable state, are known to increase the susceptibility of individuals to stroke.

It is desirable to develop treatments for cerebrovascular disease, including cerebral hemorrhage, cerebral ischemia, ischemic stroke, hemorrhagic stroke, and ischemic reperfusion injury arising from reintroduction of blood flow following cerebral ischemia or ischemic stroke.

SUMMARY OF THE INVENTION

The invention includes methods for treating cerebrovascular disease. In one aspect, the invention includes a method for treating cerebral ischemia, cerebral hemorrhage, ischemic stroke, hemorrhagic stroke, or ischemic reperfusion injury resulting from reintroduction of blood flow following cerebral ischemia or ischemic stroke. A method of the invention includes administering one or more therapeutic compounds such as pyridoxal-5'-phosphate, pyridoxine, pyridoxal, and pyridoxamine.

In another aspect, the invention is directed to a method for treating cerebral ischemia, cerebral hemorrhage, ischemic stroke, hemorrhagic stroke, or ischemic reperfusion injury resulting from reintroduction of blood flow following cerebral ischemia or ischemic stroke by administering one or more therapeutic compounds such as 3-acylated analogues of pyridoxal, 3-acylated analogue of pyridoxal-4,5-aminal, or a pharmaceutical composition thereof.

In another aspect, the invention is directed to a method for treating cerebral ischemia, cerebral hemorrhage, ischemic stroke, hemorrhagic stroke, or ischemic reperfusion injury resulting from reintroduction of blood flow following cerebral ischemia or ischemic stroke by administering one or more therapeutic compounds such as pyridoxine phosphonate analogues, or a pharmaceutical composition thereof.

In another aspect, the invention is directed to pharmaceutical compositions that include a pharmaceutically acceptable carrier and a therapeutically effective amount of a therapeutic compound selected from pyridoxal-5'-phosphate, pyridoxal, pyridoxine, pyridoxamine, 3-acylated analogues of pyridoxal, 3-acylated analogues of pyridoxal-4,5-aminal, pyridoxine phosphonate analogues, or pharmaceutically acceptable salts thereof, for treating a cerebral vascular disease.

DESCRIPTION OF THE INVENTION

Figure 1:
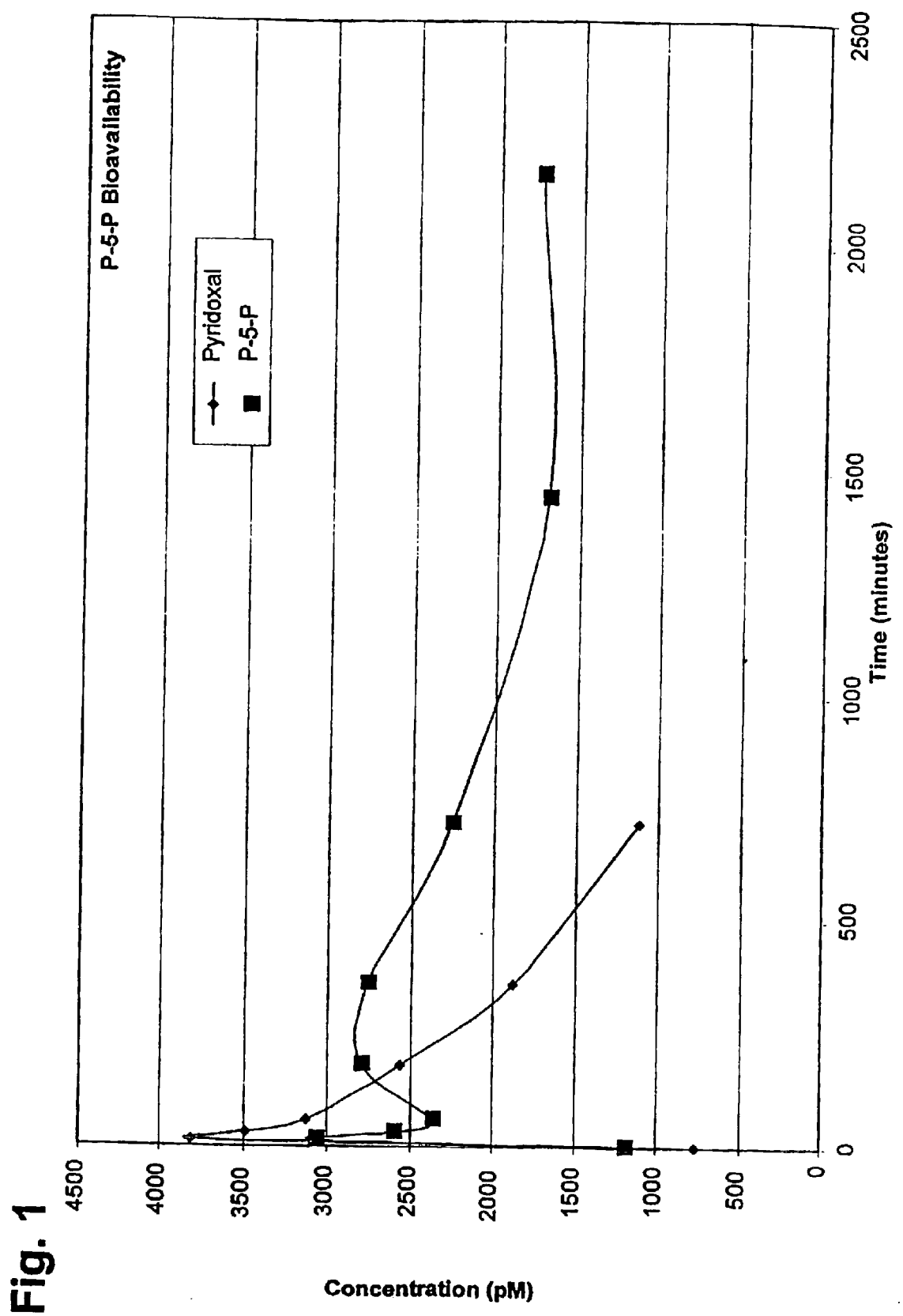
FIG. 1 shows pyridoxal and pyridoxal-5'-phosphate plasma levels in rats after administration of pyridoxal-5'-phosphate.
Figure 2:
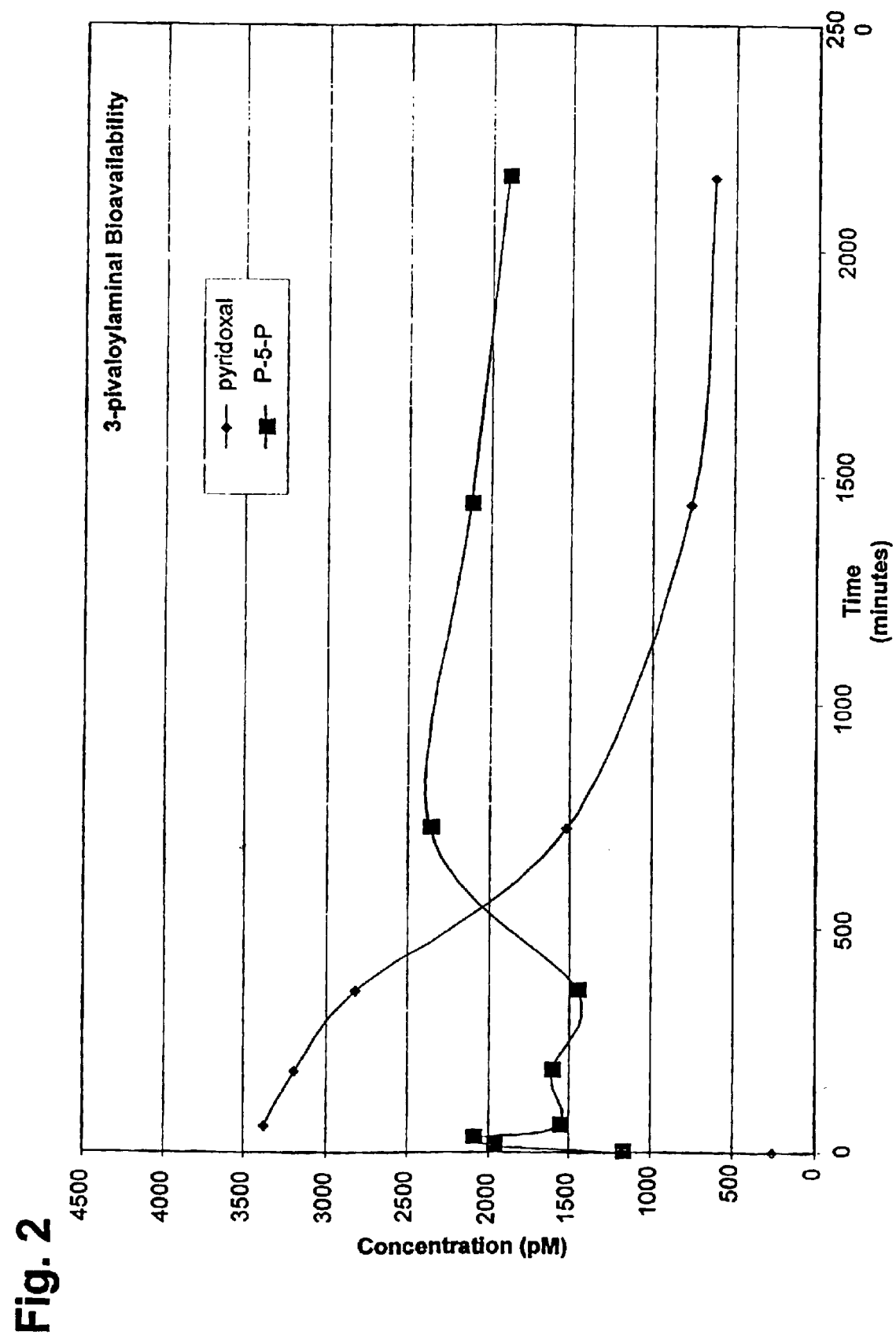
FIG. 2 shows pyridoxal and pyridoxal-5'-phosphate plasma levels in rats after administration of 3-pivaloylaminal.
Figure 3:
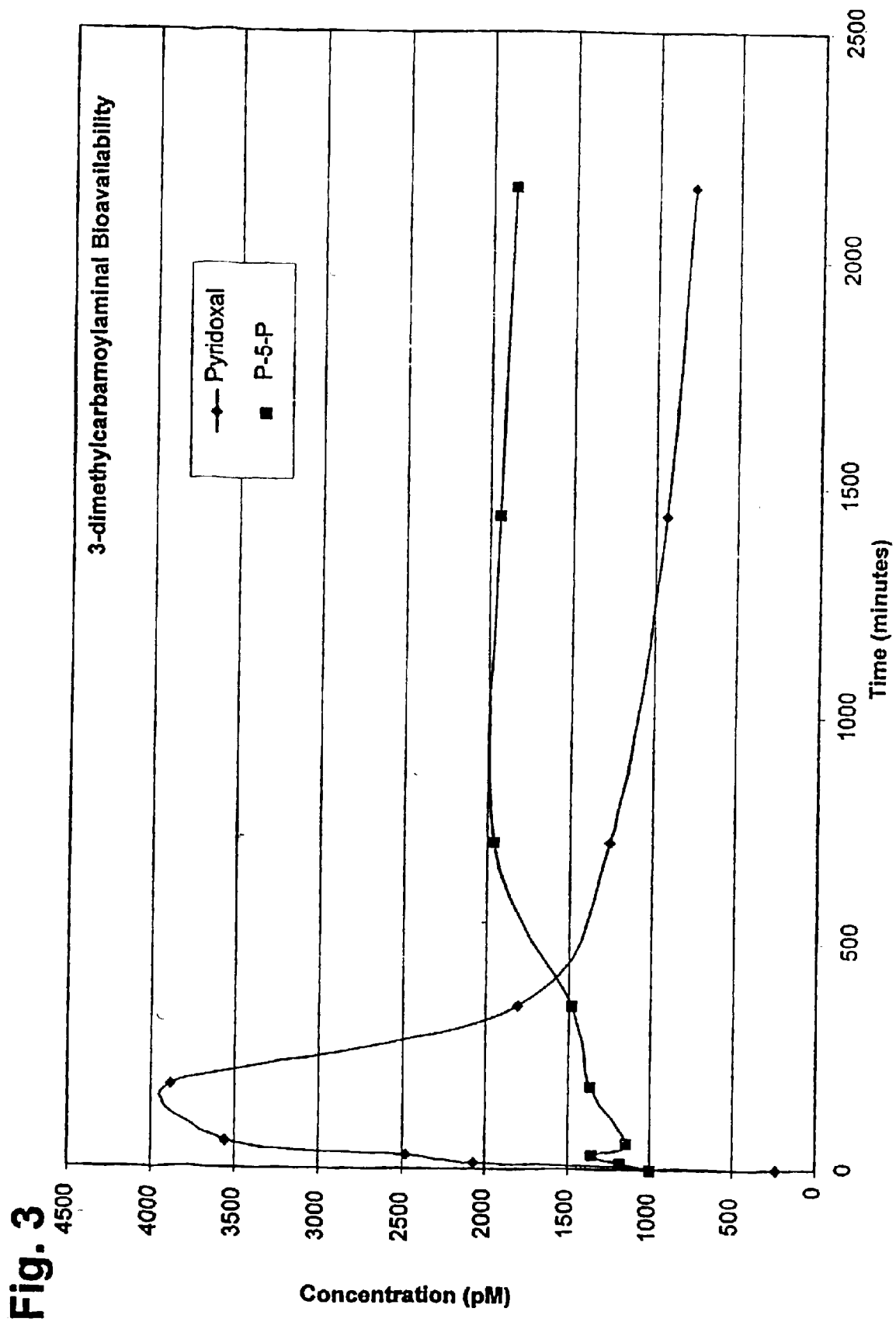
FIG. 3 shows pyridoxal and pyridoxal-5'-phosphate plasma levels in rats after administration of 3-dimethylcarbamoylaminal.
Figure 4:
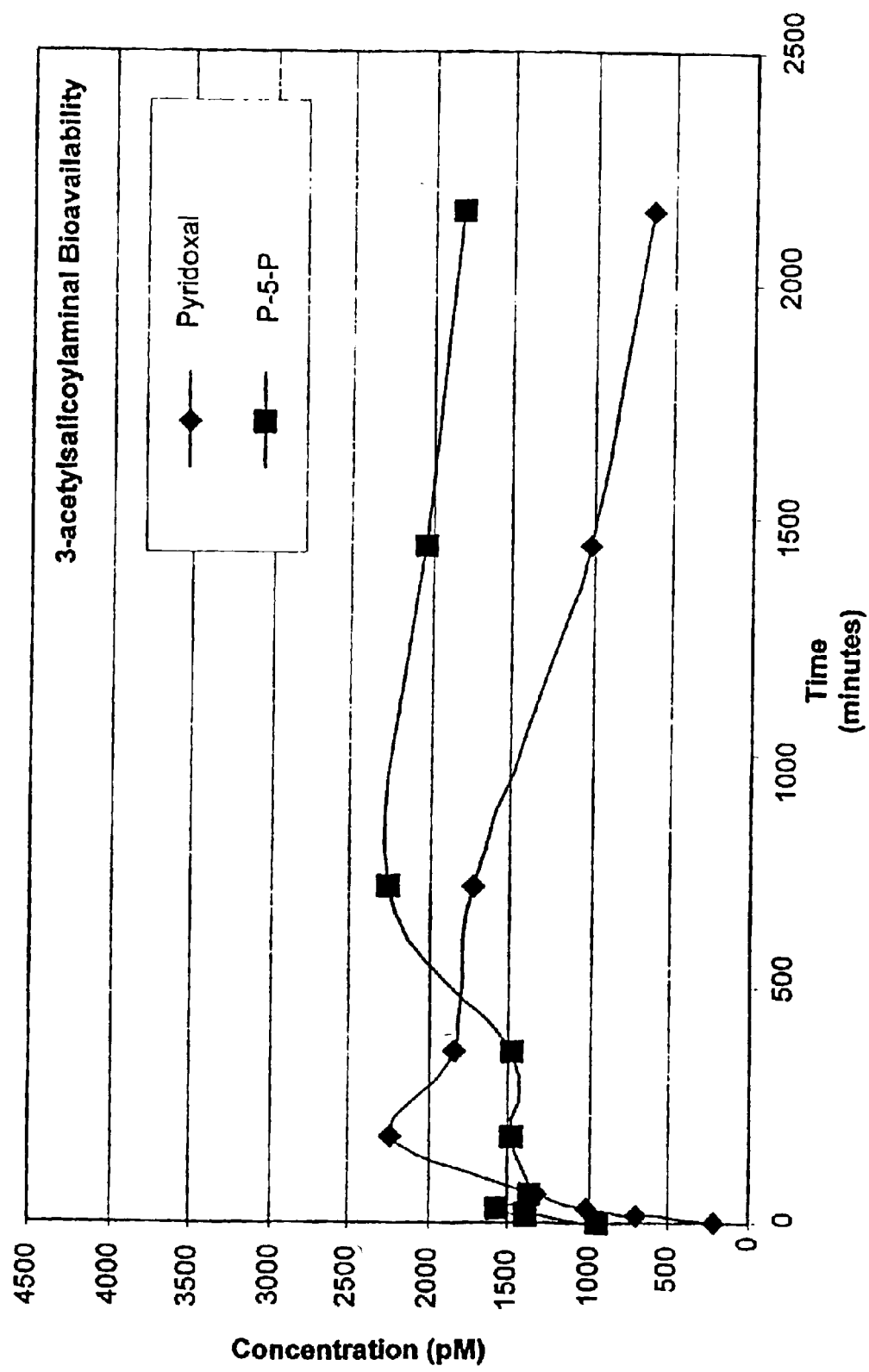
FIG. 4 shows pyridoxal and pyridoxal-5'-phosphate plasma levels in rats after administration of 3-acetylsalicoylaminal.

The recitation of numerical ranges by endpoints includes all numbers and fractions subsumed within that range (e.g. 1 to 5 includes 1, 1.5, 2, 2.75, 3, 3.80, 4, and 5).

All numbers and fractions thereof are presumed to be modified by the term "about."

It is to be understood that "a," "an," and "the" include plural referents unless the content clearly dictates otherwise. Thus, for example, reference to a composition containing "a compound" includes a mixture of two or more compounds.

Some of the compounds described herein contain one or more asymmetric centers and may thus give rise to enantiomers, diasteriomers, and other stereoisomeric forms which may be defined in terms of absolute stereochemistry as (R)- or (S)-. The present invention is meant to include all such possible diasteriomers and enantiomers as well as their racemic and optically pure forms. Optically active (R)- and (S)- isomers may be prepared using chiral synthons or chiral reagents, or resolved using conventional techniques. When the compounds described herein contain olefinic double bonds or other centers of geometric asymmetry, and unless specified, otherwise, it is intended that the compounds include both E and A geometric isomers. Likewise all tautomeric forms are intended to be included.

The invention is directed to methods of treating cerebrovascular disease by administering pyridoxal-5'-phosphate (PLP, and also called P5P), pyridoxal, pyridoxine, pyridoxamine, 3-acylated analogues of pyridoxal, 3-acylated analogue of pyridoxal-4,5-aminal, pyridoxine phosphonate analogues, or a pharmaceutical composition thereof.

Cerebrovascular disease as used herein includes, for example, any abnormality of the brain resulting from a pathologic process of a blood vessel. A pathologic process of a blood vessel includes any one or more of the following: an occlusion of a blood vessel lumen by thrombus or embolus, a rupture of a blood vessel, an altered permeability of a blood-vessel wall, and increased viscosity or other change in the quality of blood.

Examples of cerebrovascular disease include cerebral ischemia, cerebral hemorrhage, ischemic stroke, hemorrhagic stroke, and ischemia reperfusion injury resulting from reintroduction of blood flow following cerebral ischemia or ischemic stroke.

Ischemia is a condition in which an organ or a part of the body fails to receive a sufficient blood supply. When an organ is deprived of a blood supply, it is said to be hypoxic. An organ will become hypoxic even when the blood supply temporarily ceases, such as during a surgical procedure or during temporary artery blockage. Ischemia initially leads to a decrease in or loss of contractile activity. When cerebral ischemia is of sufficient severity and duration, cell injury can progress to cell death.

When blood flow resumes to an organ after temporary cessation, this is known as ischemic reperfusion of the organ. Conditions observed with ischemia reperfusion injury include neutrophil infiltration, necrosis, and apoptosis.

Although this invention is not limited to any particular theory, an analogue according to the invention can be advantageous for absorption and concentration. To enhance absorption from the digestive tract and across biological membranes, polar groups on a drug molecule can be blocked with lipophilic functions that will be enzymatically cleaved off from the drug after absorption into the circulatory system. Lipophilic moieties can also improve site-specificity and bioavailability of the drug. The speed at which the blocking groups are removed can be used to control the rate at which the drug is released. The blocking of polar groups on the drug can also slow first-pass metabolism and excretion. Phenolic hydroxy groups are particularly susceptible to glucoronidation and/or sulfonation, reactions that often precede excretion. To reduce metabolism and excretion of phenolic drugs, an ester can be used. An ester is a common blocking group that is readily hydrolyzed from the drug by endogenous esterases. Bundgaard, *Design and Application of Prodrugs* in *A Textbook of Drug Design and Development* Ch. 5 (Krogsgaard-Larson & Bundgaard, eds., Hardwood Academic Publishers, Reading, United Kingdom 1991).

Pyridoxal-5'-phosphate, pyridoxal, pyridoxine, pyridoxamine, 3-acylated analogues of pyridoxal, 3-acylated analogue of pyridoxal-4,5-aminal, pyridoxine phosphonate analogues, or pharmaceutical compositions thereof can be used in the treatment of the above-identified diseases. "Treatment" and "treating" as used herein include preventing, inhibiting, and alleviating cerebrovascular diseases and related symptoms as well as healing the ischemia-related conditions or symptoms thereof affecting the brain.

For treatments of the invention, a therapeutic compound including any one or more of pyridoxal-5'-phosphate (PLP, and also called P5P), pyridoxal, pyridoxine, pyridoxamine, 3-acylated analogues of pyridoxal, 3-acylated analogue of pyridoxal-4,5-aminal, pyridoxine phosphonate analogues, or pharmaceutical compositions thereof can be administered in a therapeutically effective amount to a patient before, during and after any above-mentioned condition arises.

A "therapeutically effective amount" as used herein includes a prophylactic amount, for example, an amount effective for preventing or protecting against cerebrovascular disease or symptoms thereof and amounts effective for alleviating or healing cerebrovascular disease or symptoms thereof. For example, a therapeutically effective amount includes an amount suitable for preventing or protecting against cerebral ischemia, cerebral hemorrhage, ischemic stroke, hemorrhagic stroke, or ischemic reperfusion injury resulting from reintroduction of blood flow following ischemic stroke or cerebral ischemia. Moreover, a therapeutically effective amount includes an amount suitable for alleviating or healing cerebral ischemia, cerebral hemorrhage, ischemic stroke, hemorrhagic stroke, or ischemic reperfusion injury resulting from reintroduction of blood flow following ischemic stroke or cerebral ischemia.

A therapeutic compound can be administered prior to ischemia to prevent, inhibit, or protect against ischemia reperfusion injury to the brain. In an alternative embodiment, a composition of the invention can be administered during or following ischemia (including during or following reperfusion) to alleviate or heal ischemia reperfusion injury of the brain.

In one aspect, the invention is directed to a method of treating cerebrovascular disease such as, for example, cerebral ischemia, cerebral hemorrhage, ischemic stroke, hemorrhagic stroke, and ischemia reperfusion injury resulting from reintroduction of blood flow following cerebral ischemia or ischemic stroke in mammals comprising administering to the mammal a therapeutically effective amount of a therapeutic compound.

Therapeutic Compounds Suitable for Use in Methods of the Invention

In one embodiment, a therapeutic compound includes any one or more of pyridoxal-5'-phosphate, pyridoxal, pyridoxine, pyridoxamine, or a pharmaceutically acceptable salt thereof.

Pyridoxal-5'-phosphate (PLP), an end product of vitamin $B_6$ metabolism, plays a vital role in mammalian health. Vitamin $B_6$ typically refers to pyridoxine, which is chemically known as 2-methyl-3-hydroxy-4,5-di(hydroxymethyl) pyridine and is represented by formula I:

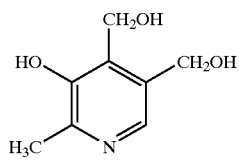

Yet two additional compounds, pyridoxal of formula II

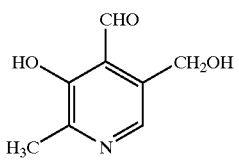

and pyridoxamine of formula III

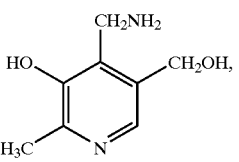

are also referred to as vitamin $B_6$. All three compounds serve as precursors to pyridoxal-5'-phosphate (PLP), which is chemically known as 3-hydroxy-2-methyl-5-[(phosphonooxy)methyl]-4-pyridine-carboxaldehyde and is represented by formula IV:

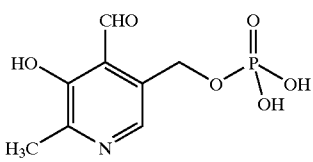

PLP is the biologically active form of vitamin $B_6$ inside cells and in blood plasma. Mammals cannot synthesize PLP de novo and must rely on dietary sources of the precursors pyridoxine, pyridoxal, and pyridoxamine, which are metabolized to PLP. For instance, mammals produce PLP by phosphorylating pyridoxine by action of pyridoxal kinase and then oxidizing the phosphorylated product.

PLP is a regulator of biological processes and a cofactor in more than 100 enzymatic reactions. It has been shown to be an antagonist of a purinergic receptor, thereby affecting ATP binding; it has been implicated in modulation of platelet aggregation; it is an inhibitor of certain phosphatase enzymes; and it has been implicated in the control of gene transcription. PLP is also a coenzyme in certain enzyme-catalyzed processes, for example, in glycogenolysis at the glycogen phosphorylase level, in the malate asparatate shuttle involving glycolysis and glycogenolysis at the transamination level, and in homocysteine metabolism. In previous patents (U.S. Pat. No. 6,051,587 and U.S. Pat. No. 6,043,259) the role of pyridoxal-5'-phosphate, and its precursors pyridoxal and pyridoxine (vitamin $B_6$), in mediating cardiovascular health and in treating cardiovascular related diseases has been disclosed.

Therapeutic compounds also include any one or more of the 3-acylated analogues of pyridoxal represented by formula V:

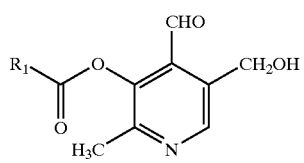

where $R_1$ is alkyl, alkenyl, in which alkyl or alkenyl can be interrupted by nitrogen, oxygen, or sulfur, and can be unsubstituted or substituted at the terminal carbon with hydroxy, alkoxy, alkanoyloxy, alkanoyloxyaryl, alkoxyalkanoyl, alkoxycarbonyl, or R1 is dialkylcarbamoyloxy; alkoxy; dialkylamino; alkanoyloxy; alkanoyloxyaryl; alkoxyalkanoyl; alkoxycarbonyl; dialkylcarbamoyloxy; or R1 is aryl, aryloxy, arylthio, or aralkyl, in which aryl can be substituted by alkyl, alkoxy, amino, hydroxy, halo, nitro, or alkanoyloxy;

or a pharmaceutically acceptable salt thereof.

The term "alkyl" includes a straight or branched saturated aliphatic hydrocarbon radicals, such as, for example, methyl, ethyl, propyl, isopropyl (1-methylethyl),

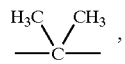

butyl, tert-butyl (1,1-dimethylethyl), and the like.

The term "alkenyl" includes an unsaturated aliphatic hydrocarbon chain having from 2 to 8 carbon atoms, such as, for example, ethenyl, 1-propenyl, 2-propenyl, 1-butenyl, 2-methyl-1-propenyl, and the like.

The above alkyl or alkenyl can optionally be interrupted in the chain by a heteroatom, such as, for example, a nitrogen, sulfur, or oxygen atom, forming an alkylaminoalkyl, alkylthioalkyl, or alkoxyalkyl, for example, methylaminoethyl, ethylthiopropyl, methoxymethyl, and the like.

The above alkyl or alkenyl can optionally be substituted at the terminal carbon by hydroxy, alkoxy, alkanoyloxyaryl, alkanoyloxy, alkoxyalkanoyl, alkoxycarbonyl, or dialkylcarbamoyloxy.

The term "alkoxy" (i.e. alkyl-O—) includes alkyl as defined above joined to an oxygen atom having preferably from 1 to 4 carbon atoms in a straight or branched chain, such as, for example, methoxy, ethoxy, propoxy, isopropoxy (1-methylethoxy), butoxy, tert-butoxy (1,1-dimethylethoxy), and the like.

The term "dialkylamino" includes two alkyl groups as defined above joined to a nitrogen atom, in which alkyl has preferably 1 to 4 carbon atoms, such as, for example, dimethylamino, diethylamino, methylethylamino, methylpropylamino, diethylamino, and the like.

The term "alkanoyloxy" includes a group of the formula

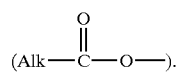

Examples of alkanoyloxy include methanoyloxy, ethanoyloxy, propanoyloxy, and the like. Examples of alkyl substituted at the terminal carbon by alkanoyloxy include 1-ethanoyloxy-1-methylethyl, propanoyloxy-1-methylethyl, and the like.

The term "alkanoyloxyaryl" includes a group of the formula

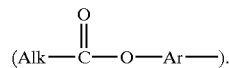
(Alk—C(=O)—O—Ar—).

Examples of alkanoyloxyaryl include methanoyloxyphenyl, ethanoyloxyphenyl, propanoyloxyphenyl, and the like.

The term "aryl" refers to unsaturated aromatic carbocyclic radicals having a single ring, such as phenyl, or multiple condensed rings, such as naphthyl or anthryl. The term "aryl" also includes substituted aryl comprising aryl substituted on a ring by, for example, $C_{1-4}$ alkyl, $C_{1-4}$ alkoxy, amino, hydroxy, phenyl, nitro, halo, carboxyalkyl or alkanoyloxy. Aryl groups include, for example, phenyl, naphthyl, anthryl, biphenyl, methoxyphenyl, halophenyl, and the like.

The term "aryloxy" (i.e. aryl-O—) includes aryl having an oxygen atom bonded to an aromatic ring, such as, for example, phenoxy and naphthoxy.

The term "arylthio" (i.e. aryl-S—) includes aryl having a sulfur atom bonded to an aromatic ring, such as, for example, phenylthio and naphthylthio.

The term "aralkyl" refers to an aryl radical defined as above substituted with an alkyl radical as defined above (e.g. aryl-alkyl-). Aralkyl groups include, for example, phenethyl, benzyl, and naphthylmethyl.

Aryl from any of aryl, aryloxy, arylthio, aralkyl, and alkanoyloxyaryl can be unsubstituted or can be substituted on a ring by, for example, $C_{1-4}$ alkyl, $C_{1-4}$ alkoxy, amino, hydroxy, nitro, halo, or alkanoyloxy. Examples of substituted aryl include toluyl, methoxyphenyl, ethylphenyl, and the like.

The term "alkoxyalkanoyl" includes a group of the formula

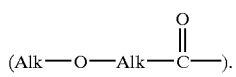
(Alk—O—Alk—C(=O)—).

Examples of alkoxyalkanoyl include (2-acetoxy-2-methyl) propanyl, 3-ethoxy-3-propanoyl, 3-methoxy-2-propanoyl, and the like.

The term "alkoxycarbonyl" includes a group of the formula

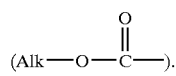
(Alk—O—C(=O)—).

Examples of alkoxycarbonyl include methoxycarbonyl, ethoxycarbonyl, propoxycarbonyl, and the like.

The term "dialkylcarbamoyloxy" includes a group of the formula

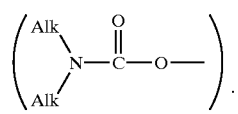

Examples of dialkylcarbamoyloxy include dimethylaminomethanoyloxy, 1-ethyl-1-methylaminomethanoyloxy, and the like. Examples of alkyl substituted at the terminal carbon by alkanoyloxy include dimethylamino-1-methylethyl, 1-ethyl-1-methylamino-methanoyloxy-1-methlethyl, and the like.

The term "halo" includes bromo, chloro, and fluoro.

$R_1$ groups for compounds of formula V can be toluyl, naphthyl, phenyl, phenoxy, dimethylamino, 2,2-dimethylethyl, ethoxy, (2-acetoxy-2-methyl)propanyl, 1-ethanoyloxy-1-methylethyl, tert-butyl, acetylsalicyl, and ethanoyloxyphenyl.

Preferred $R_1$ groups for compounds of formula V are toluyl or naphthyl. Such $R_1$ groups when joined with a carbonyl group form an acyl group

$R_1C(=O)—$ which preferred for compounds of formula V include toluoyl or β-naphthoyl. Of the toluoyl group, the p-isomer is more preferred.

Examples of 3-acylated analogues of pyridoxal include, but are not limited to, 2-methyl-3-toluoyloxy-4-formyl-5-hydroxymethylpyridine and 2-methyl-β-naphthoyloxy-4-formyl-5-hydroxymethylpyridine.

Therapeutic compounds also include any one or more of the 3-acylated analogues of pyridoxal-4,5-aminal represented by formula VI:

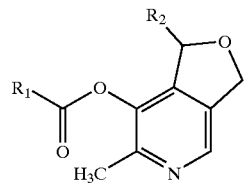

VI where $R_1$ is alkyl, alkenyl, in which alkyl or alkenyl can be interrupted by nitrogen, oxygen, or sulfur, and can be unsubstituted or substituted at the terminal carbon with hydroxy, alkoxy, alkanoyloxy, alkanoyloxyaryl, alkoxyalkanoyl, alkoxycarbonyl, or dialkylcarbamoyloxy; or $R_1$ is alkoxy; dialkylamino; alkanoyloxy; alkanoyloxyaryl; alkoxyalkanoyl; alkoxycarbonyl; dialkylcarbamoyloxy; or $R_1$ is aryl, aryloxy, arylthio, or aralkyl, in which aryl can be substituted by alkyl, alkoxy, amino, hydroxy, halo, nitro, or alkanoyloxy;

$R_2$ is a secondary amino group;

or a pharmaceutically acceptable salt thereof.

The terms "alkyl," "alkenyl," "alkoxy," "dialkylamino," "alkanoyloxy," "alkanoyloxyaryl," "alkoxyalkanoyl," "alkoxycarbonyl," "dialkylcarbamoyloxy," "halo," "aryl," "aryloxy," "arylthio," and "aralkyl" are as defined above for formula VI.

The term "secondary amino" group includes a group of formula VII:

VII

derived from a secondary amine $R_3R_4NH$, in which $R_3$ and $R_4$ are each independently alkyl, alkenyl, cycloalkyl, aryl, or, when $R_3$ and $R_4$ are taken together, may form a ring with the nitrogen atom and which may be interrupted by a heteroatom, such as, for example, a nitrogen, sulfur, or oxygen atom. The terms "alkyl," "alkenyl," and "aryl" are used as defined above in forming secondary amino groups such as, for example, dimethylamino, methylethylamino, diethylamino, dialkylamino, phenylmethylamino, diphenylamino, and the like.

The term "cycloalkyl" refers to a saturated hydrocarbon having from 3 to 8 carbon atoms, preferably 3 to 6 carbon atoms, such as, for example, cyclopropyl, cyclopentyl, cyclohexyl, and the like.

When $R_3$ and $R_4$ are taken together to form a ring with the nitrogen atom, a cyclic secondary amino group, such as, for example, piperidino, can be formed. And, when the cyclic secondary amino group is interrupted with a heteroatom, a group such as, for example, piperazino or morpholino can be formed.

$R_1$ groups for compounds of formula VI can be toluyl, naphthyl, phenyl, phenoxy, dimethylamino, 2,2-dimethylethyl, ethoxy, (2-acetoxy-2-methyl)propanyl, 1-ethanoyloxy-1-methylethyl, tert-butyl, acetylsalicyl, and ethanoyloxyphenyl.

Preferred $R_1$ groups for compounds of formula VI include toluyl, e.g., p-toluyl, naphthyl, tert-butyl, dimethylamino, acetylphenyl, hydroxyphenyl, or alkoxy, e.g., methoxy. Such $R_1$ groups when joined with a carbonyl group form an acyl group

which preferred for compounds of formula VI include toluoyl, β-naphthoyl, pivaloyl, dimethylcarbamoyl, acetylsalicyloyl, salicyloyl, or alkoxycarbonyl. A preferred secondary amino group may be morpholino.

Examples of 3-acylated analogues of pyridoxal-4,5-aminal include, but are not limited to, 1-morpholino-1,3-dihydro-7-(p-toluoyloxy)-6-methylfuro(3,4-c)pyridine; 1-morpholino-1,3-dihydro-7-(β-naphthoyloxy)-6-methylfuro(3,4-c)pyridine; 1-morpholino-1,3-dihydro-7-pivaloyloxy-6-methylfuro(3,4-c)pyridine; 1-morpholino-1,3-dihydro-7-carbamoyloxy-6-methylfuro(3,4-c)pyridine; and 1-morpholino-1,3-dihydro-7-acetylsalicyloxy-6-methylfuro(3,4-c)pyridine.

Therapeutic compounds include any one or more pyridoxal phosphonate analogues represented by the formula VIII:

VIII

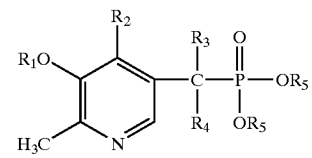

where
$R_1$ is hydrogen or alkyl;
$R_2$ is —CHO, —CH$_2$OH, —CH$_3$, —CO$_2$R$_6$ in which $R_6$ is hydrogen, alkyl, or aryl; or
$R_2$ is —CH$_2$—O-alkyl- in which alkyl is covalently bonded to the oxygen at the 3-position instead of $R_1$;
$R_3$ is hydrogen and $R_4$ is hydroxy, halo, alkoxy, alkanoyloxy, alkylamino or arylamino; or
$R_3$ and $R_4$ are halo; and
$R_5$ is hydrogen, alkyl, aryl, aralkyl, or —CO$_2$R$_7$ in which $R_7$ is hydrogen, alkyl, aryl, or aralkyl;
or a pharmaceutically acceptable salt thereof.

The terms "alkyl," "alkoxy," "alkanoyloxy," "halo," "aryl," and "aralkyl" are as defined above for formula VI.

The term "alkylamino" refers to —NH-alkyl with alkyl as defined above. Alkylamino groups include those with 1–6 carbons in a straight or branched chain, such as, for example, methylamino, ethylamino, propylamino, and the like.

The term "arylamino" refers to —N-aryl with aryl as defined above. Arylamino includes —NH-phenyl, —NH-biphenyl, —NH-4-methoxyphenyl, and the like.

Examples of compounds of formula VIII include those where $R_1$ is hydrogen, or those where $R_2$ is —CH$_2$OH, or —CH$_2$—O-alkyl- in which alkyl is covalently bonded to the oxygen at the 3-position instead of $R_1$, or those where $R_3$ is hydrogen and $R_4$ is F, MeO— or CH$_3$C(O)O—, or those where $R_5$ is alkyl or aralkyl. Additional examples of compounds of formula VIII include those where $R_3$ and $R_4$ are F, or those where $R_5$ is t-butyl or benzyl.

Therapeutic compounds further include any one or more pyridoxal phosphonate analogues represented by the formula IX:

IX

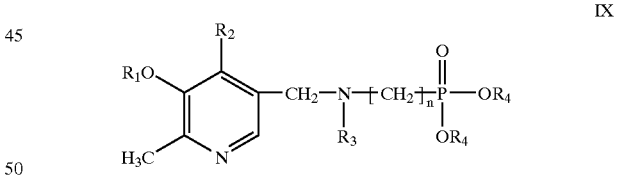

in which
$R_1$ is hydrogen or alkyl;
$R_2$ is —CHO, —CH$_2$OH, —CH$_3$ or —CO$_2$R$_5$ in which $R_5$ is hydrogen, alkyl, or aryl; or
$R_2$ is —CH$_2$—O-alkyl- in which alkyl is covalently bonded to the oxygen at the 3-position instead of $R_1$;
$R_3$ is hydrogen, alkyl, aryl, or aralkyl;
$R_4$ is hydrogen, alkyl, aryl, aralkyl, or —CO$_2$R$_6$ in which $R_6$ is hydrogen, alkyl, aryl, or aralkyl;
n is 1 to 6;
or a pharmaceutically acceptable salt thereof.

The terms "alkyl," "aryl," and "aralkyl" are as defined above for formula VI.

Examples of compounds of formula IX include those where $R_1$ is hydrogen, or those where $R_2$ is —CH$_2$OH, or —CH$_2$—O-alkyl- in which alkyl is covalently bonded to the oxygen at the 3-position instead of R$_1$, or those where R$_3$ is hydrogen, or those where R$_4$ is alkyl or hydrogen. Additional examples of compounds of formula IX include those where R$_4$ is ethyl.

Therapeutic compounds further include any one or more pyridoxal phosphonate analogues represented by the formula IX:

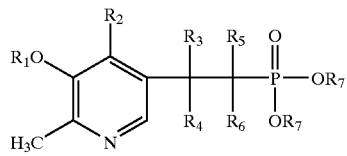

in which

R$_1$ is hydrogen or alkyl;

R$_2$ is —CHO, —CH$_2$OH, —CH$_3$ or —CO$_2$R$_8$ in which R$_8$ is hydrogen, alkyl, or aryl; or R$_2$ is —CH$_2$—O-alkyl- in which alkyl is covalently bonded to the oxygen at the 3-position instead of R$_1$;

R$_3$ is hydrogen and R$_4$ is hydroxy, halo, alkoxy or alkanoyloxy; or

R$_3$ and R$_4$ can be taken together to form =O;

R$_5$ and R$_6$ are hydrogen; or

R$_5$ and R$_6$ are halo;

R$_7$ is hydrogen, alkyl, aryl, aralkyl, or —CO$_2$R$_8$ in which R$_8$ is hydrogen, alkyl, aryl, or aralkyl;

or a pharmaceutically acceptable salt thereof.

The terms "alkyl," "alkoxy," "alkanoyloxy," "halo," "aryl," and "aralkyl" are as defined above for formula VI.

Examples of compounds of formula III include those where R$_1$ is hydrogen, or those where R$_2$ is —CH$_2$OH, or —CH$_2$—O-alkyl- in which alkyl is covalently bonded to the oxygen at the 3-position instead of R$_1$, or those where R$_3$ and R$_4$ taken together form =O or those where R$_5$ and R$_6$ are F, or those where R$_7$ is alkyl. Additional examples of compounds of formula III include those where R$_4$ is OH or CH$_3$C(O)O—, those where R$_7$ is ethyl.

Pharmaceutically acceptable salts of the compounds of formulas I, II, III, IV, V, VI, VII, IX, or X include salts derived from nontoxic inorganic acids such as hydrochloric, nitric, phosphoric, sulfuric, hydrobromic, hydriodic, hydrofluoric, phosphorus, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulphonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glutamine, etc. (see, e.g., Berge et al., *J. Pharmaceutical Science*, 66: 1–19 (1977)).

The salts of the basic compounds are prepared by contacting the free base form with a sufficient amount of a desired acid to produce the salt in the conventional manner. The free base form can be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Syntheses

To prepare a compound of formula VIII, 3,4-isopropylidenepyridoxine-5-al is treated with a phosphonating agent, such as, a metal salt of di-tert-butyl phosphite or dibenzyl phosphite or diphenyl phosphite, to give protected alpha-hydroxyphosphonates. The protected alpha-hydroxyphosphonates can be treated with an acylating agent in an aprotic solvent, such as acetic anhydride in pyridine, or with an alkylating agent, such as methyl iodide and sodium hydride in tetrahydrofuran (THF), to give alpha-alkylcarbonyloxy or alpha-alkyloxyphosphonates esters respectively. Alternatively the protected alpha-hydroxyphosphonates can be treated with an agent to convert the hydroxyl group to a halogen, such as conversion to a fluoro group with DAST (diethylaminosulfurtrifluoride), to prepare the alpha-halophosphonate esters. The isopropylidene protecting group is removed from the fully protected alpha-substituted phosphonates by reacting them with water and an acid, such as 20% water in acetic acid, to prepare the pyridoxine-alpha-substituted phosphonate esters. The ester groups can be removed from the phosphonate groups of the pyridoxine-alpha-substituted phosphonate esters by further treating them with acid in water, such as 20% water in acetic acid, to give the corresponding phosphonic acids as can be seen in the following scheme.

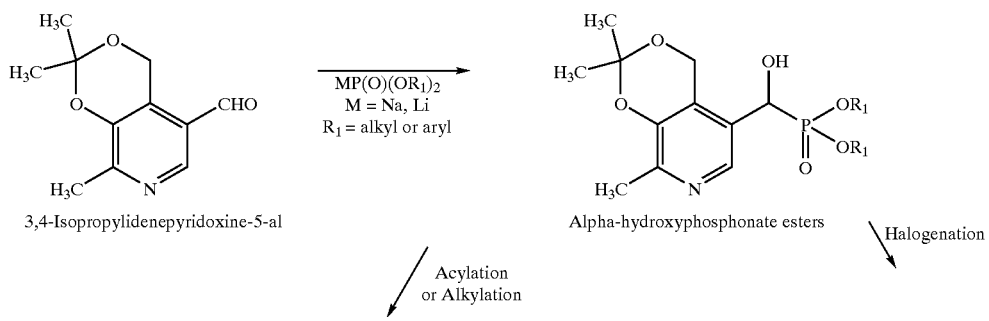

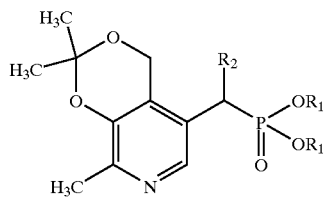

Alpha-alkyloxy or acyloxyphosphonate esters
R$_2$ = alkoxy or alkylcarbonyloxy

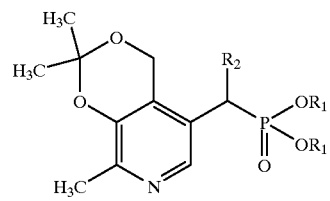

Alphahalophosphonate esters
X = halogen

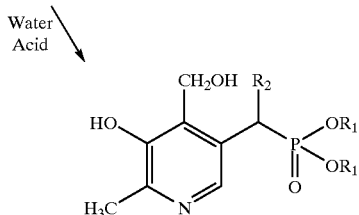

Pyridoxine-alpha-substituted phosphonate esters and acids

R$_2$ = hydroxy, halogen, alkoxy or alkylcarbonyloxy
R$_1$ = hydrogen, alkyl or aryl Alternatively, to prepare a compound of formula I, 3,4-isopropylidenepyridoxine-5-halide is treated with a phosphonating agent, such as, a metal salt of di-tert-butyl phosphite or dibenzyl phosphite or diphenyl phosphite, to give protected phosphonates. The protected phosphonates are treated with a base, such as sodium hexamethyldisilazane (NaHMDS), and a halogenating agent, such as N-fluorobenzenesulfonimide (NFSi), to provide the dihalophosphonates as can be seen in the following scheme.

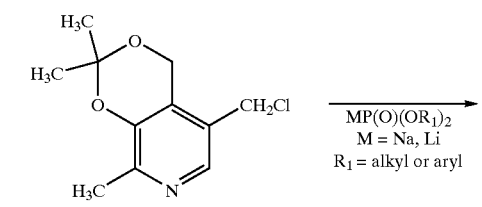

3,4-Isopropylidenepyridoxine-5-chloride

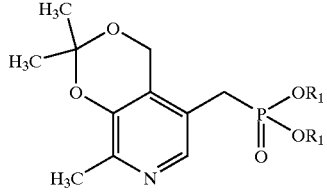

Phosphonate esters

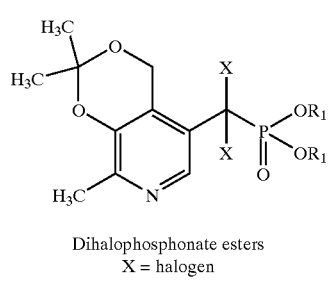

Dihalophosphonate esters
X = halogen

Alternatively, to prepare a compound of formula VIII, 3,4-isopropylidenepyridoxine-5-al is treated with an amine, such as p-methoxyaniline or p-aminobiphenyl, and a phosphonating agent, such as, a metal salt of di-tert-butyl phosphite, dibenzyl phosphite or diphenyl phosphite, to give protected aminophosphonates as can be seen in the following scheme.

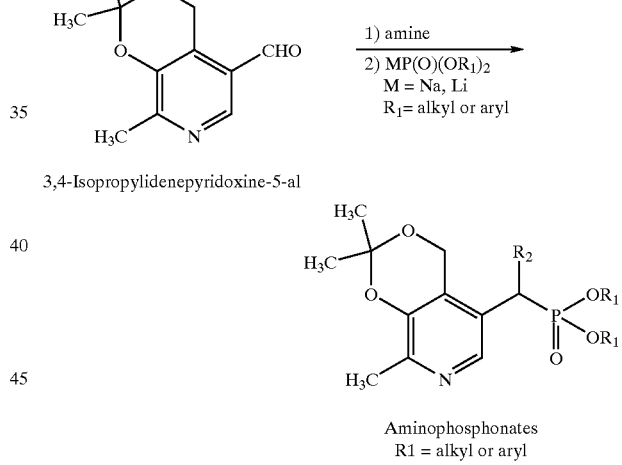

3,4-Isopropylidenepyridoxine-5-al

Aminophosphonates
R1 = alkyl or aryl
R$_2$ = N-alkyl or N-aryl

To prepare a compound of formula IX, 3,4-isopropylidenepyridoxine-5-amine is used as a starting material. The amine is treated with a haloalkylphosphonate diester, such as diethyl bromomethylphosphonate, to give 5'-phosphonoazaalkylpyridine diesters. Reaction of the 3,4-isopropylidene-5'-phosphonoazaalkylpyridoxine diesters with a trialkylsilyl halide, such as trimethylsilyl bromide, in an aprotic solvent, such as acetonitrile, removes the ester groups of the phosphonate diester to provide the corresponding free 3,4-isopropylidene-5'-phosphonoazaalkylpyridoxine diacid. The acetonide protecting group on the 3 and 4 position of the pyridoxine ring on the 3,4-isopropylidene-5'-phosphonoazaalkylpyridoxine diacid can be removed by reaction with acid and water, such as 20% water in acetic acid as can be seen in the following scheme.

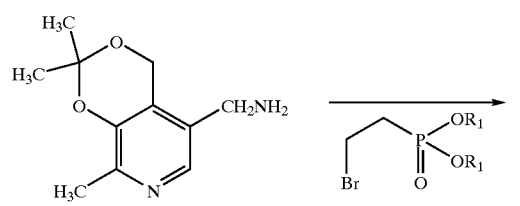

3,4-Isopropylidene pyridoxine-5-amine

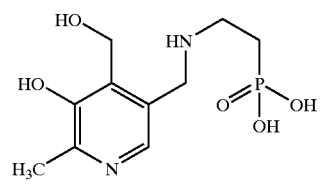

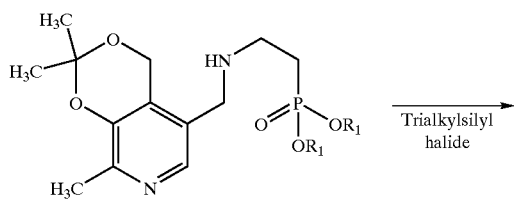

Phosphonate esters

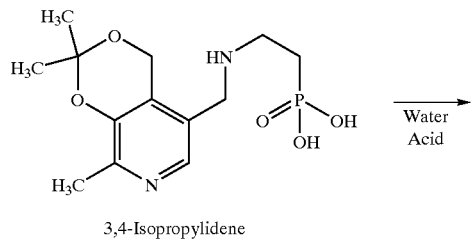

3,4-Isopropylidene
5-phosphonoazaalkylpyridoxine diacid 5-phosphonoazaalkylpyridoxine diacid To prepare a compound of formula X, 3,4-isopropylidenepyridoxine-5-al is reacted with a metal salt of a methyl, or dihalomethyl, phosphonate diester to produce 5′-phosphonoalkylpyridoxine diesters. The 5′-hydroxyl group of this product is acylated by an acylating agent, such as acetic anhydride in pyridine, to provide the corresponding O-acyl derivatives respectively, or oxidized to the keto functional group by an oxidizing agent, such as manganese dioxide. The blocking group at the 3 and 4 positions and the phosphonate ester groups of the hydroxy, alkylcarbonyloxy and keto phosphonate diesters are hydrolysed by reaction with acid and water, such as 20% water in acetic acid, to provide the corresponding phosphonate diesters, without the blocking group at the 3 and 4 position. These reactions are illustrated in the following scheme.

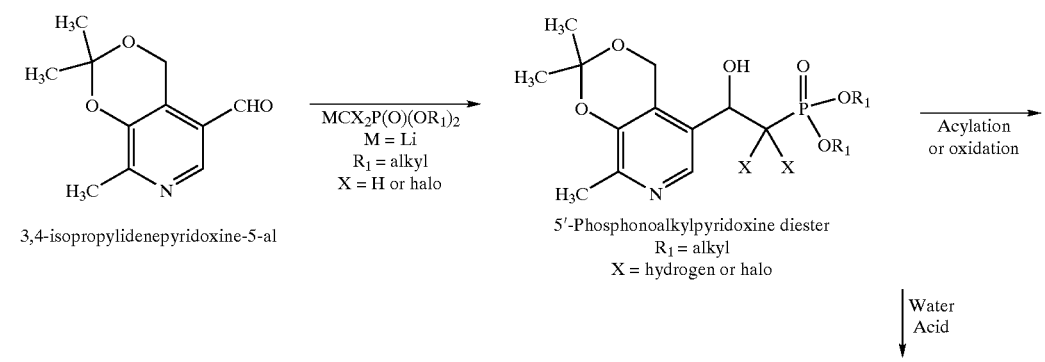

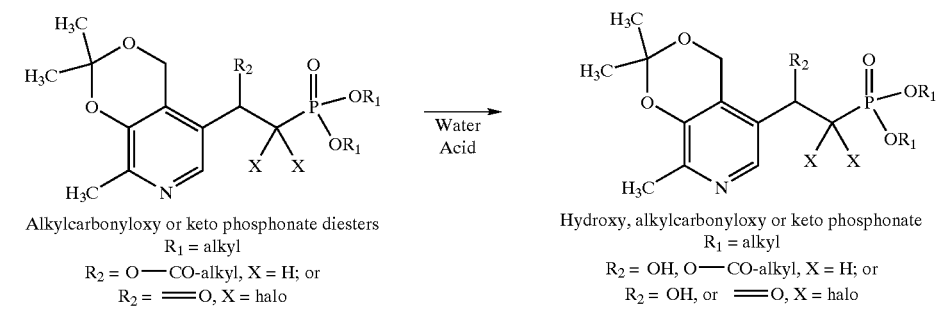

Pharmaceutical Composition Suitable for Use with Methods of the Invention

A therapeutic compound as defined above can be formulated into a pharmaceutical composition for use in methods of the invention. A pharmaceutical composition is suitable for treatment of cerebral hemorrhage, cerebral ischemia, ischemic stroke, hemorrhagic stroke, and ischemic reperfusion injury arising from reintroduction of blood flow following cerebral ischemia or ischemic stroke.

A pharmaceutical composition comprises a pharmaceutically acceptable carrier and a therapeutic compound of formula I, II, III, IV, V, VI, VII, IX, or X or a pharmaceutically acceptable salt thereof. A pharmaceutically acceptable carrier includes, but is not limited to, physiological saline, ringers, phosphate-buffered saline, and other carriers known in the art. Pharmaceutical compositions can also include additives, for example, stabilizers, antioxidants, colorants, excipients, binders, thickeners, dispersing agents, readsorpotion enhancers, buffers, surfactants, preservatives, emulsifiers, isotonizing agents, and diluents. Pharmaceutically acceptable carriers and additives are chosen such that side effects from the pharmaceutical compound are minimized and the performance of the compound is not canceled or inhibited to such an extent that treatment is ineffective. Preferably the compound selected is PLP.

Methods of preparing pharmaceutical compositions containing a pharmaceutically acceptable carrier and therapeutic compound of formula I, II, III, IV, V, VI, VII, IX, or X or a pharmaceutically acceptable salt thereof are known to those of skill in the art.

All methods can include the step of bringing the compound of the invention in association with the carrier and additives. The formulations generally are prepared by uniformly and intimately bringing the compound of the invention into association with a liquid carrier or a finely divided solid carrier or both, and then, if necessary, shaping the product into the desired unit dosage form.

Generally, a solution of a therapeutic compound, for example PLP, may be prepared by simply mixing PLP with a pharmaceutically acceptable solution, for example, buffered aqueous saline solution at a neutral or alkaline pH (because PLP is essentially insoluble in water, alcohol, and ether), at a temperature of at least room temperature and under sterile conditions. Preferably, the PLP solution is prepared immediately prior to administration to the mammal. However, if the PLP solution is prepared at a time more than immediately prior to the administration to the mammal, the prepared solution should be stored under sterile, refrigerated conditions. Furthermore, because PLP is light sensitive, the PLP solution should be stored in containers suitable for protecting the PLP solution from the light, such as amber-colored vials or bottles.

A pharmaceutical composition or therapeutic compound can be administered enterally or parenterally. Parenteral administration includes subcutaneous, intramuscular, intradermal, intramammary, intravenous, and other administrative methods known in the art. Enteral administration includes solution, tablets, sustained release capsules, enteric coated capsules, and syrups. When administered, the pharmaceutical composition or therapeutic compound should be at or near body temperature.

Methods of Treatment

A physician or veterinarian of ordinary skill readily determines a subject who is exhibiting symptoms of any one or more of the diseases described above. Regardless of the route of administration selected, the therapeutic compounds of formula I, II, III, IV, V, VI, VII, IX, or X or a pharmaceutically acceptable salt thereof can be formulated into pharmaceutically acceptable unit dosage forms by conventional methods known to the pharmaceutical art. An effective but nontoxic quantity of the compound is employed in treatment.

The therapeutic compound of formula I, II, III, IV, V, VI, VII, IX, or X or a pharmaceutically acceptable salt thereof can be administered in enteral unit dosage forms, such as, for example, tablets, sustained-release tablets, enteric coated tablets, capsules, sustained-release capsules, enteric coated capsules, pills, powders, granules, solutions, and the like. They can also be administered parenterally, such as, for example, subcutaneously, intramuscularly, intradermally, intramammarally, intravenously, and other administrative methods known in the art.

Although it is possible for a therapeutic compound of formula I, II, III, IV, V, VI, VII, IX, or X or a pharmaceutically acceptable salt thereof as described above to be administered alone in a unit dosage form, preferably the compound is administered in admixture as a pharmaceutical composition.

The ordinarily skilled physician or veterinarian will readily determine and prescribe the therapeutically effective amount of the therapeutic compounds of formula I, II, III, IV, V, VI, VII, IX, or X or a pharmaceutically acceptable salt thereof to treat the disease for which treatment is administered. In so proceeding, the physician or veterinarian could employ relatively low dosages at first, subsequently increasing the dose until a maximum response is obtained. Typically, the particular disease, the severity of the disease, the compound to be administered, the route of administration, and the characteristics of the mammal to be treated, for example, age, sex, and weight, are considered in determining the effective amount to administer. Administering a therapeutic amount of a compound of the invention for treating cerebrovascular disease such as, for example, cerebral hemorrhage, cerebral ischemia, ischemic stroke, hemorrhagic stroke, and ischemic reperfusion injury arising from reintroduction of blood flow following cerebral ischemia or ischemic stroke; or symptoms thereof, is in a range of about 0.1–100 mg/kg of a patient's body weight, more preferably in the range of about 0.5–50 mg/kg of a patient's body weight, per daily dose. The compound can be administered for periods of short and long duration. Although some individual situations can warrant to the contrary, short-term administration, for example, 30 days or less, of doses larger than 25 mg/kg of a patient's body weight is preferred to long-term administration. When long-term administration, for example, months or years, is required, the suggested dose should not exceed 25 mg/kg of a patient's body weight.

A therapeutically effective amount of a therapeutic compound of formula I, II, III, IV, V, VI, VII, IX, or X or a pharmaceutically acceptable salt thereof for treating the above-identified diseases or symptoms thereof can be administered prior to, concurrently with, or after the onset of the disease or symptom.

The therapeutic compound of formula I, II, III, IV, V, VI, VII, IX, or X or a pharmaceutically acceptable salt thereof can be administered to treat one or more cerebrovascular diseases.

A therapeutically effective amount of a therapeutic compound of formula I, II, III, IV, V, VI, VII, IX, or X or a pharmaceutically acceptable salt thereof to treat cerebral hemorrhage, cerebral ischemia, ischemic stroke, hemorrhagic stroke, and ischemic reperfusion injury arising from reintroduction of blood flow following cerebral ischemia or ischemic stroke is typically in the range of about 0.5–100 mg/kg of a patient's body weight, more preferably in the range of about 0.5–50 mg/kg of a patient's body weight, per daily dose. The compound may be administered for periods of short and long durations depending on the condition treated.

A therapeutically effective amount of the therapeutic compound for treating cerebral ischemia-related conditions can be administered before, during, or following ischemia (including during or following reperfusion), as well as continually for some period spanning from pre- to post-ischemia. Additionally, the therapeutic compound may be taken on a regular basis to protect against cellular dysfunction arising from arrhythmia and heart failure.

A therapeutic compound can be administered concurrently with compounds that are already known to be suitable for treating the above-identified diseases. Concurrent administration" and "concurrently administering" as used herein includes administering a therapeutic compound and a known therapy for cerebrovascular disease in admixture such as, for example, in a pharmaceutical composition or in solution, or as separate components, such as, for example, separate pharmaceutical compositions or solutions administered consecutively, simultaneously, or at different times but not so distant in time such that the therapeutic compound and the known therapy cannot interact and a lower dosage amount of the active ingredient cannot be administered. Preferably the cerebrovascular disease treated is ischemic stroke.

Compounds useful in treating cerebrovascular disease that can be concurrently administered with therapeutic compounds of formulae I, II, III, IV, V, VI, VII, IX, or X or a pharmaceutically acceptable salt thereof include clot dissolving compounds, anti-platelet or blood thinning compounds, neuroprotective compounds and ion channel blockers. Useful clot dissolving compounds include, for example, plasminogen activator (rtPA) and prourokinase. Useful anti-platelet or blood thinning compounds include, for example, aspirin, dipyridamole, clopidogrel, and GPIIb/IIIa inhibitors. Useful neuroprotective compounds include, for example, citicoline, clomethiazole, piracetam, and ebselen. Useful ion channel blockers include, for example, sipatrigine.

This invention will be further characterized by the following examples. These examples are not meant to limit the scope of the invention, which has been fully set forth in the foregoing description. Variations within the scope of the invention will be apparent to those skilled in the art.

EXAMPLES

All reagents used in the following Examples can be purchased from Aldrich Chemical Company (Milwaukee, Wis. or Allentown, Pa.).

Example 1

Synthesis of di-t-butyl ($\alpha^4$,3-O-isopropylidene-3-hydroxy-4-hydroxymethyl-2-methyl-5-pyridyl)hydroxymethylphosphonate Di-tert-butyl phosphite (16.3 g, 84 mmol) was added to a solution of NaH (3.49 g, 60%, 87.2 mmol) in THF (60 mL) under nitrogen at 0° C. The temperature of the resulting solution was raised to room temperature and the solution stirred for 15 min, then cooled to 0° C. again. To this solution, ($\alpha^4$,3-O-isopropylidene-3-hydroxy-4-hydroxymethyl-2-methyl-5-pyridyl)methanal (Kortynk et al., J. Org. Chem., 29, 574–579 (1964)) (11.41 g, 55.05 mmol) in THF (30 mL) was slowly added then the temperature raised to room temperature again and stirring continued for 2 h. The reaction was quenched by adding saturated NaHCO$_3$ (40 ml), and diluted with diethyl ether (200 mL). The ether layer was separated, washed with saturated aqueous NaHCO$_3$ (40 ml, 5%), then saturated brine (3×20 mL). The ether layer was dried (MgSO$_4$), filtered and evaporated to give crude product as a colorless solid. This solid was washed with hexane to remove the oil (from the NaH) and unreacted phosphite. The solid was recrystallized from a mixture of diethylether:hexane:ethyl acetate (230 mL:70 mL:15 mL). The colorless crystal (17.9 g, 81%) were filtered and washed with hexane.

$^1$H NMR (CDCl$_3$): 1.42 (9H, d), 1.46 (9H, d), 1.51 (6H, d), 2.38 (3H, s), 4.70 (1H, d), 4.89–5.13 (2H, m), 8.11 (1H, s).

$^{31}$P NMR (H-decoupled, CDCl$_3$): 13.43 (s).

This structure can be represented by formula:

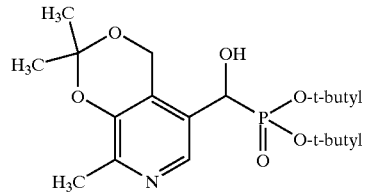

Example 2

Synthesis of dibenzyl ($\alpha^4$,3-O-isopropylidene-3-hydroxy-4-hydroxymethyl-2-methyl-5-pyridyl)hydroxymethylphosphonate Dibenzyl phosphite (1.89 g, 9.62 mmol) was mixed with the ($\alpha^4$,3-O-isopropylidene-3-hydroxy-4-hydroxymethyl-2-methyl-5-pyridyl)methanal (Kortynk et al., J. Org. Chem., 29, 574–579 (1964)) (1.00 g, 4.81 mmol) and stirred at room temperature for an hour. To this thick syrup was added activated basic alumina (1 g). The reaction mixture was then stirred at 80° C. for one hour. The reaction mixture was diluted with dichloromethane (50 mL), and filtered through Celite to remove alumina. The dichloromethane solution was washed with saturated, aqueous NaHCO$_3$ (20 mL), then saturated brine (3×10 mL). The dichloromethane layer was dried (MgSO$_4$), filtered and evaporated to give crude product as a colorless solid. The crude product was purified by silica gel column chromatography, using ether:hexanes (1:2) as eluent to give 1.3 g (58%).

$^1$H NMR (CDCl$_3$): 1.30 (3H, s), 1.45 (3H, s), 2.30 (3H, s), 4.86–4.99 (7H, s), 7.18–8.07 (10H, s), 8.08 (1H, s).

This structure can be represented by formula:

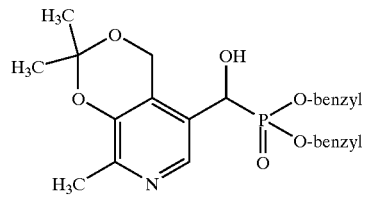

Example 3

Synthesis of (3-hydroxy-4-hydroxymethyl-2-methyl-5-pyridyl)hydroxymethyl Phosphonic Acid The product of Example 1 above, of formula V, (10 g, 24.9 mmol) was dissolved in acetic acid (80% in water, 100 ml) and heated at 60° C. for 1 d. Colorless precipitate was formed, however, the reaction was not complete. Another 50 ml of 80% acetic acid in water was added to the mixture and the mixture stirred at 60° C. for another day. The solid was filtered off, washed with cold water, then methanol and dried to give a colorless solid (4.78 g, 77%).

$^1$H NMR (D$_2$O): 2.47 (3H, s), 4.75–4.79 (2H, m), 5.15–5.19 (1H, d), 7.82 (1H, s).

$^{31}$P NMR (H-decoupled D$_2$O): 14.87 (s).

This structure can be represented by formula:

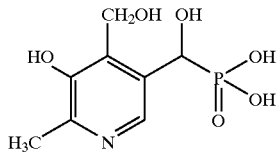

Example 4
Synthesis of dibenzyl ($\alpha^4$,3-O-isopropylidene-3-hydroxy-4-hydroxymethyl-2-methyl-5-pyridyl)fluoromethylphosphonate The protected alpha-hydroxy phosphonate from Example 2 above of structure VI (1.0 g, 2.49 mmol) was dissolved in dichloromethane (10 mL), and the solution cooled to −78° C. To this solution was added diethylaminosulfurtrifluoride (DAST) (0.8 g, 4.98 mmol). The reaction was stirred at −78° C. under nitrogen for 20 minutes then allowed to stand at room temperature overnight. The reaction mixture was diluted with dichloromethane (50 ml), and washed with saturated, aqueous NaHCO$_3$ (125 mL). The dichloromethane layer was dried (MgSO$_4$), filtered and evaporated to give crude fluorophosphonate as a yellow solid. The crude product was purified by silica gel column chromatography, using ethyl acetate:hexanes (2:1) as the eluent to give 600 mg (60%).

$^1$H NMR (CDCl$_3$): 1.42 (3H, s), 1.52 (3H, s), 2.40 (3H, s), 4.91–4.97 (6H, m), 5.46–5.61 (1H, dd), 7.23–7.34 (10H, m), 8.01 (1H, s).

$^{31}$P NMR (H-decoupled, F-coupled, CDCl$_3$): 16.36–16.08 (d).

This structure can be represented by formula:

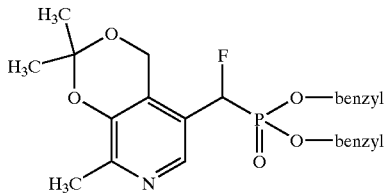

Example 5
Synthesis of di-t-butyl ($\alpha^4$,3-O-isopropylidene-3-hydroxy-4-hydroxymethyl-2-methyl-5-pyridyl)fluoromethylphosphonate The protected alpha-hydroxy phosphonate from Example 1 of structure V (3 g, 7.55 mmol) was dissolved in dichloromethane (30 mL), and the solution cooled to −78° C. To this solution was added diethylaminosulfurtrifluoride (DAST) (1.22 g, 7.57 mmol). The reaction was stirred at −78° C. under nitrogen for 5 minutes, quenched by addition of saturated, aqueous NaHCO$_3$ (2 mL) then allowed to warm to room temperature. The reaction mixture was diluted with dichloromethane (50 ml), and washed with saturated, aqueous NaHCO$_3$ (2×20 mL). The dichloromethane layer was dried (MgSO$_4$), filtered and evaporated to give crude fluorophosphonate. The crude product was purified by silica gel column chromatography, using ethyl acetate:hexanes (1:1) as the eluent to give 350 mg (12%).

$^1$H NMR (CDCl$_3$): 1.44 (9H, s), 1.46 (9H, s), 1.52 (3H, s), 1.56 (3H, s), 2.41 (3H, s), 4.98–5.14 (2H, m), 5.32–5.52 (1H, dd), 8.03 (1H, s).

$^{31}$P NMR (H-decoupled, F-coupled, CDCl$_3$): 6.53, 7.24.

$^{19}$F NMR (H-decoupled, CDCl$_3$): −202.6, −203.0

This structure can be represented by formula:

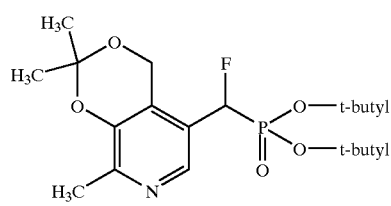

Example 6
Synthesis of di-t-butyl (3-hydroxy-4-hydroxymethyl-2-methyl-5-pyridyl)fluoromethyl Phosphonate The protected di-t-butyl alpha-fluoro phosphonate from Example 5 of structure IX (3.2 g 7.8 mmol) was dissolved in acetic acid (80% in water, 50 ml) and heated at 60° C. for 24 hours. The pale yellow solid was filtered off, washed with cold water and methanol, and then dried to give a creamy solid (2.21 g, 70%).

$^1$H NMR (CDCl$_3$): 1.41 (9H, s), 1.44 (9H, s), 1.49 (3H, s), 1.51 (3H, s), 2.42 (3H, s), 4.99–5.07 (2H, m), 5.33–5.51 (1H, d,d), 8.04 (1H, s).

$^{31}$P NMR (H-decoupled, F-Coupled, CDCl$_3$): 7.10–7.80 (d).

$^{19}$F NMR (H, P-Coupled, CDCl$_3$): −203.07 to −202.61 (dd).

This structure can be represented by formula:

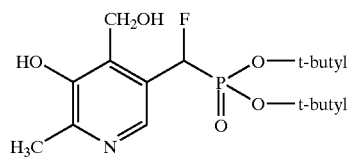

Example 7
Synthesis of (3-hydroxy-4-hydroxymethyl-2-methyl-5-pyridyl)fluoromethyl Phosphonic Acid The protected di-t-butyl alpha-fluoro phosphonate from Example 5 of structure IX (200 mg, 0.5 mmol) was dissolved in acetic acid (80% in water, 15 ml) and heated at 75° C. for 24 hours. The solvent was removed by evaporation on a rotary evaporator using toluene to codistill the water. The crude product (183 mg) was purified by column chromatography on silica using chloroform:methanol:water (65:35:2) as eluent to give 60 mg (55%).

$^1$H NMR (D$_2$O): 2.46 (3H, bs), 4.65–4.90 (2H, dd), 5.81–6.01 (1H, dd), 7.74 (1H, bs).

$^{31}$P NMR (H-decoupled, F-Coupled, CDCl$_3$): 9.3 (d).

$^{19}$F NMR (H, P-Coupled, CDCl$_3$): −197 to −196 (dd).

This structure can be represented by formula:

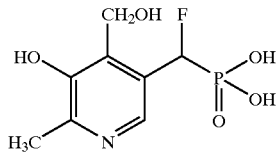

Example 8
Synthesis of di-t-butyl (α⁴,3-O-isopropylidene-3-hydroxy-4-hydroxymethyl-2-methyl-5-pyridyl)acetoxymethylphosphonate The product of Example 1 above, of formula V (1.0 g, 2.49 mmol) was dissolved in dichloromethane (20 mL), the solution cooled to −5° C., and pyridine (2 mL) added, followed by acetic anhydride (1 mL). The reaction temperature was slowly allowed to reach room temperature. After one hour, the reaction was quenched by adding dilute aqueous hydrochloric acid (10%, 75 mL), and then diluted with dichloromethane (25 mL). After separation of the aqueous layer the methylene chloride layer washed with saturated $NaHCO_3$ (2×20 mL). The dichloromethane layer was dried ($MgSO_4$), filtered and evaporated to give crude alpha acetoxy phosphonate as a colorless solid. The crude product was purified by silica gel column chromatography, using ethyl acetate:hexanes (2:1) as the eluent to give the product in good yield.

$^1$H NMR ($CDCl_3$): 1.31 (9H, d), 1.36 (9H, d), 1.49 (6H, d), 2.1 (3H s), 2.38 (3H, s), 5.04 (2H, d), 5.72–5.76 (1H, d), 8.11 (1H, s).

$^{31}$P NMR (H-decoupled, $CDCl_3$): 13.43 (s).

This structure can be represented by formula:

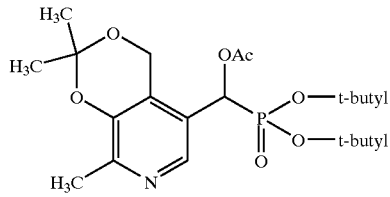

Example 9
Synthesis of di-t-butyl (α⁴,3-O-isopropylidene-3-hydroxy-4-hydroxymethyl-2-methyl-5-pyridyl)methoxymethylphosphonate The product of Example 1 above, of formula V (300 mg, 0.75 mmol) was dissolved in 15 ml of THF and reaction vessel was purged with $N_2$ gas. Sodium hydride (21 mg, 0.9 mmol) was added, and the solution stirred for 5 minutes before cooling to 0° C. Methyl iodide (160 mg, 1.1 mmol) was then injected and reaction vessel was gradually allowed to reach room temperature. TLC (ethyl acetate) indicated that the reaction was complete in 3 hours. The soution was diluted with methylene chloride (250 mL), washed with dilute, aqueous HCL (10%, 100 mL), then saturated, aqueous $NaHCO_3$, dried ($MgSO_4$) and evaporated. The crude product was chromatographed on silica gel using ethyl acetate/hexanes (1:1) as the eluent to give 132 mg (32%).

$^1$H NMR ($CDCl_3$): 1.41 (18H, s), 1.51 (3H, s), 1.54 (3H, s), 2.40 (3H, s), 3.33 (3H, s), 4.20–4.26 (1H, d), 5.05 (2H, bs), 8.01 (1H, s).

$^{31}$P NMR (H-decoupled, $CDCl_3$): 10.88 (s).

This structure can be represented by formula:

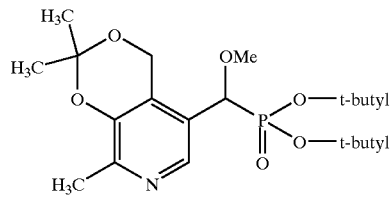

Example 10
Synthesis of (3-hydroxy-4-hydroxymethyl-2-methyl-5-pyridyl)acetoxymethyl Phosphonic Acid The product of Example 8 above, of formula XII, (50 mg, 0.11 mmol) was added to acetic acid (80% in water) and stirred for 24 hours at 60° C. The solvent was removed by evaporation on a rotary evaporator using toluene to codistill the water. The crude product was purified by chromatography on silica gel column using $CH_2Cl_2$/MeOH/$H_2O$ (65:35:4) as eluent to give 22.8 mg (76%).

$^1$H NMR ($D_2O$): 2.23 (3H, s), 2.51 (3H, s), 4.6–5.1 (2H, m), 6.1 (1H, d), 7.85 (1H, s).

This structure can be represented by formula:

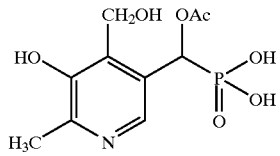

Example 11
Synthesis of (3-hydroxy-4-hydroxymethyl-2-methyl-5-pyridyl)methoxymethyl Phosphonic Acid The product of Example 9 above, of formula XIII (132 mg, 0.32 mmol) was dissolved in acetic acid (80% in water, 25 mL) and stirred at 60° C. for 24 hours. The solvent was removed by evaporation on a rotary evaporator using toluene to codistill the water. The crude product was purified by chromatography on silica gel column using $CH_2Cl_2$/MeOH/$H_2O$ (65:35:4) as eluent to give the product in good yield.

$^1$H NMR ($D_2O$): 2.52 (3H, s), 3.32 (3H, s), 4.47–4.88 (2H, m), 7.87 (1H, s).

$^{31}$P NMR (H-decoupled, $D_2O$): 13.31 (s)

This structure can be represented by formula:

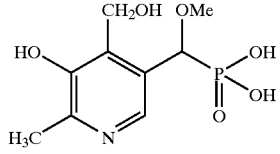

Example 12
Synthesis of dibenzyl (α⁴,3-O-isopropylidene-3-hydroxy-4-hydroxymethyl-2-methyl-5-pyridyl)difluoromethylphosphonate To a solution of dibenzyl (α⁴,3-O-isopropylidene-3-hydroxy-4-hydroxymethyl-2-methyl-5-pyridyl) methylphosphonate (115 mg, 0.253 mmol) in THF (10 mL) was added NaHMDS (1 M, 0.56 mL, 0.56 mmol). The reaction mixture was cooled to −78° C. After 15 minutes, NFSi (237 mg, 0.75 mmol) was added to the reaction mixture. The temperature of the reaction mixture was slowly warmed to −20° C. The solution was diluted with Et₂O, washed with saturated NaHCO₃, water and brine, dried (MgSO₄) and evaporated. The crude product was chromatographed on silica using ethyl acetate:hexanes (2:1) as eluent to give the dibenzyl (α⁴,3-O-isopropylidene-3-hydroxy-4-hydroxymethyl-2-methyl-5-pyridyl)difluoromethylphosphonate in good yields.

¹H NMR (CDCl₃) 1.53 (s, 6H), 2.45 (d, 3H), 5.34 (d, 2H), 7.09–7.39 (m, 14H), 8.29 (s,1H).
³¹P NMR (CDCl₃) −2.15 (t).
¹⁹F NMR (CDCl₃) −105.7 (d).

This structure can be represented by formula:

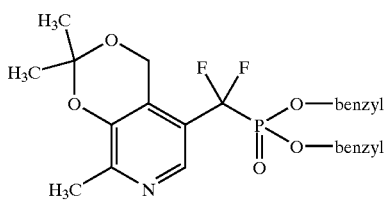

Example 13
Synthesis of di-t-butyl (α⁴,3-O-isopropylidene-3-hydroxy-4-hydroxymethyl-2-methyl-5-pyridyl)(4-biphenylamino)methylphosphonate The (α⁴,3-O-isopropylidene-3-hydroxy-4-hydroxymethyl-2-methyl-5-pyridyl)methanal (Kortynk et al., J. Org. Chem., 29, 574–579 (1964)) (424 mg, 2.19 mmol) and 4-aminobiphenyl (360 mg, 2.12 mmol) was refluxed in benzene (20 mL) under nitrogen, using a Dean-Stark trap to remove water, for 15 hours. The crude reaction mixture was evaporated, dissolved in THF (20 mL) and added to a flask containing di-t-butyl phosphite (955 mg, 5.12 mmol) in THF (20 mL) and NaH (270 mg, 57% in oil, 6.41 mmol) and stirred at 0° C. for two hours. The solution was diluted with Et₂O, washed with saturated, aqueous NaHCO₃ (40 mL), brine (20 mL), dried (MgSO₄) and evaporated. The crude product was chromatographed on silica gel using hexane:diethyl ether (2:1) to give di-t-butyl (α⁴,3-O-isopropylidene-3-hydroxy-4-hydroxymethyl-2-methyl-5-pyridyl)(4-biphenylamino)methylphosphonate in modest yields.

¹H NMR (CDCl₃) 8.40 (1H, d,), 7.50–7.41 (2H, m), 7.40–7.30 (4H, m), 7.28–7.10 (1H, m), 6.54 (1H, d), 5.24 (1H, dd,), 5.07 (1H, dd,), 4.65 (1H, dd,),4.44 (1H, dd,), 2.40 (3H, d), 1.58 (3H, s), 1.49 (3H, s), 1.43 (9H, s), 1.41 (9H, s).
³¹P NMR (H-decoupled, CDCl₃): 13.1 (s).

This structure can be represented by formula:

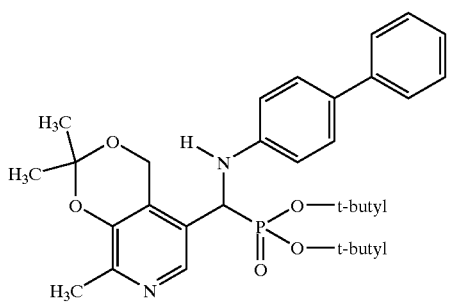

Example 14
Synthesis of di-t-butyl (α⁴,3-O-isopropylidene-3-hydroxy-4-hydroxymethyl-2-methyl-5-pyridyl)(4-methoxyphenylamino)methylphosphonate (α⁴,3-O-Isopropylidene-3-hydroxy-4-hydroxymethyl-2-methyl-5-pyridyl)methanal (Kortynk et al., J. Org. Chem., 29, 574–579 (1964)) (2.5 g, 12.1 mmol) and 4-aminoanisole (1.41 g, 11.4 mmol) was refluxed in benzene (100 mL) under nitrogen, using a Dean-Stark trap to remove water, for 15 hours. The reaction mixture was evaporated to give 3.02 g of crude imine. The crude imine (370 mg, 1.19 mmol) was dissolved in THF (20 mL) and added to a flask containing di-t-butyl phosphite (955 mg, 5.1 mmol) in THF (20 mL) and NaH (208 mg, 57% in oil, 4.94 mmol) and stirred at 0° C. for two hours and at room temperature for 24 hours. The solution was diluted with Et₂O, washed with saturated, aqueous NaHCO₃ (40 mL), brine (40 mL), dried (MgSO₄) and evaporated. The crude product was chromatographed on silica gel using hexane:diethyl ether (2:1) to give di-t-butyl (α⁴,3-O-isopropylidene-3-hydroxy-4-hydroxymethyl-2-methyl-5-pyridyl)(4-methoxyphenylamino)methylphosphonate in modest yields.

¹H NMR (CDCl₃) 8.09 (1H, d), 6.70–6.60 (2H, m), 6.47–6.36 (2H, m), 5.18 (1H, dd), 4.98 (1H, dd), 4.36–4.20 (2H, m), 3.65 (3H, s), 2.35 (3H, s), 1.54 (3H, s), 1.45 (3H, s), 1.39 (9H, s), 1.38 (9H, s).
³¹P NMR (decoupled, CDCl₃): δ 13.5 ppm.

This structure can be represented by formula:

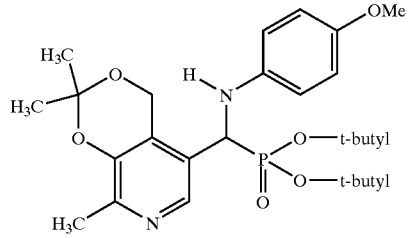

Example 15
Synthesis of di-t-butyl (α⁴,3-O-isopropylidene-3-hydroxy-4-hydroxymethyl-2-methyl-5-pyridyl)-3-azabutylphosphonate (α⁴,3-O-Isopropylidene-3-hydroxy-4-hydroxymethyl-2-methyl-5-pyridyl)methylbromide (Imperalli et al, J. Org. Chem., 60, 1891–1894 (1995)) (1.08 g. 4.0 mmol) in anhydrous DMF (20 ml) was treated with sodium azide (260 mg, 4.0 mmol) at room temperature. After one hour stirring at room temperature, the solution was extracted with diethyl ether (5×20 mL). The combined extracts were washed with water (10 mL), and brine (10 mL) and dried (MgSO₄). The solvent was evaporated and the crude product was purified by chromatography on silica gel using ethyl ether:hexanes (2:1) as eluent to give the azide as a colorless liquid (552 mg, 60%).

¹H NMR (CDCl3, TMS) 1.57 (s, 6H), 2.42 (s, 3H), 4.23 (s, 2H), 4.86 (s, 2H), 7.96 (s, 1H).

The purified azide (100 mg, 0.4 mmol) was dissolved in 95% ethanol and hydrogenated at 1 atm in presence of Lindlar catalyst (50 mg) for one hour. The catalyst was removed by filtration (Celite), and the solvent removed to give the crude amine. Purification by chromatography on silica gel using CH₂Cl₂:MeOH (5:1) as eluent gave the product (80 mg, 82%) 1HNMR (CD₂Cl₂) 1.53 (s, 6H), 2.34 (s, 3H), 3.72 (s, 2H), 4.91 (s, 2H), 5.31 (s, 2H), 7.93 (s, 1H).

The (α⁴,3-O-Isopropylidene-3-hydroxy-4-hydroxymethyl-2-methyl-5-pyridyl)methylamine, from above, (416 mg, 2 mmol) was heated in saturated, aqueous sodium bicarbonate solution (10 mL) to 95° C., followed by slow addition of diethyl 2-bromoethylphosphonate (0.09 mL, 0.5 mmol) and the reaction stirred at 95° C. overnight. The solution is evaporated using toluene to codistill the water. The crude product is triturated with ethyl acetate to dissolve the crude organic product. Chromatography on silica gel using methylene chloride:methanol:hexanes (5:1:5) gave 76 mg (41%).

$^1$Hnmr (CDCl$_3$, TMS) 1.27 (t, 6H), 1.51 (s, 6H), 1.91 (t, 2H), 2.35 (s, 3H), 2.85 (t, 2H), 3.62 (s, 2H), 4.03 (m, 4H), 4.91 (s, 2H), 7.88 (s, 1H).

$^{31}$P NMR (H-decoupled, CDCl$_3$): 31.00 (s).

This structure can be represented by formula:

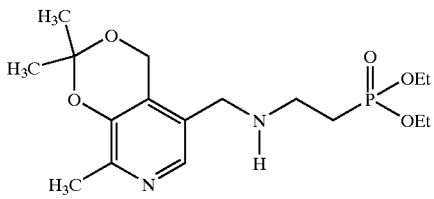

Example 16

Synthesis of ($\alpha^4$,3-O-isopropylidene-3-hydroxy-4-hydroxymethyl-2-methyl-5-pyridyl)-3-azabutylphosphonic Acid The product of Example 15, of formula XIX (280 mg, 0.75 mmol) was stirred in a mixture of acetonitile (6 mL) and trimethylsilylbromide (TMSBr) (574 mg, 3.75 mmol) overnight at room temperature. The solvent was evaporated and the crude product was purified by chromatography on silica gel using dichloromethane:methanol:water (65:35:6) giving 188 mg (91%).

$^1$H NMR (D$_2$O) 1.65 (s, 6H), 2.02 (m,2H), 2.42 (s,3H), 3.40 (m, 2H), 4.24 (s, 2H), 5.12 (s, 2H), 8.11 (s, 1H).

$^{31}$P NMR (H-decoupled, D$_2$O): 18.90 (s).

This structure can be represented by formula:

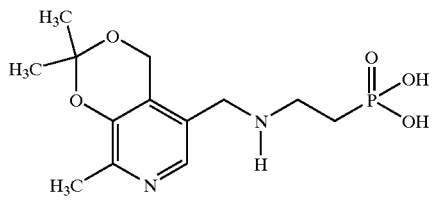

Example 17

Synthesis of (3-hydroxy-4-hydroxymethyl-2-methyl-5-pyridyl)-3-azabutylphosphonic Acid The product of Example 16, of formula XX (168 mg, 0.53 mmol) was dissolved in acetic acid (80% in water, 10 mL) and heated to 60° C. for 5 hours. The solvent was removed by evaporation using toluene to codistill the water. The crude product was purified by chromatography on C-18 reverse phase silica gel using methanol:water (4:1) as eluent to give 57 mg (39%).

$^1$H NMR (D$_2$O) 2.05 (m, 2H), 2.52 (s, 3H), 3.38 (m, 2H), 4.42 (s, 2H), 4.96 (s, 2H), 7.87 (s, 1H).

$^{31}$P NMR (H-decoupled, D$_2$O): 18.90 (s).

This structure can be represented by formula:

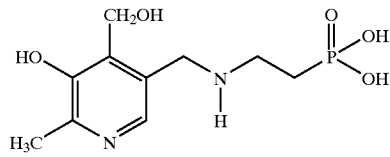

Example 18

Synthesis of diethyl ($\alpha^4$,3-O-isopropylidene-3-hydroxy-4-hydroxymethyl-2-methyl-5-pyridyl)-2-hydroxyethylphosphonate To a solution of diethyl methyl phosphite (0.29 mL, 2 mmol) in THF (20 mL) was added BuLi (2.5 M in hexane, 0.88 mL, 2.2 mmol), followed by ($\alpha^4$,3-O-isopropylidene-3-hydroxy-4-hydroxymethyl-2-methyl-5-pyridyl)methanal (Kortynk et al., J. Org. Chem., 29, 574–579 (1964)) (414 mg, 2 mmol) and the reaction mixture stirred at −78° C. for two hours. The solution was evaporated, dissolved in dichloromethane (50 mL), washed with saturated, aqueous NaHCO$_3$, dried (MgSO$_4$), evaporated and purified by chromatography on silica gel using ethyl acetate:hexane (1:2) as eluent to give 625 mg (87%).

$^1$H NMR(CDCl$_3$, TMS) 1.33 (m, 6H), 1.54 (s, 6H), 2.20 (m, 2H), 2.38 (s, 3H), 4.12 (m, 4H), 4.94 (s, 2H), 4.94 (s, 2H), 5.04 (t, 1H), 8.02 (s, 1H).

$^{31}$P NMR (H-decoupled, CDCl$_3$): 29.03 (s).

This structure can be represented by formula:

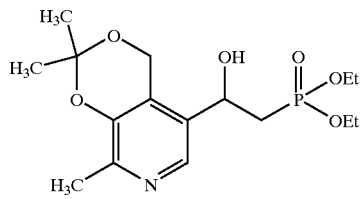

Example 19

Synthesis of diethyl ($\alpha^4$,3-O-isopropylidene-3-hydroxy-4-hydroxymethyl-2-methyl-5-pyridyl)-2acetoxyethylphosphonate The product of Example 18, of structure XXII (300 mg, 0.84 mmol) was acetylated in pyridine (0.5 mL) and acetic anhydride (0.25 mL) at 0° C. for 5 minutes followed by 3 hours at room temperature. The solvent was removed by evaporation using toluene to codistill the solvents and the crude product was dissolved in dichloromethane (10 mL). This was washed with dilute HCl (10%, 5 mL), then saturated, aqueous NaHCO$_3$, dried (MgSO$_4$) and evaporated. Chromatography on silica gel using ethyl acetate:hexane (1:1) gave 258 mg (71%).

$^1$H NMR(CDCl$_3$, TMS) 1.21 (m, 6H), 1.54 (s, 6H), 2.03 (s,3H), 3.97 (m, 4H), 5.07 (dd, 2H), 5.83 (dd, 1H), 8.02 (s, 1H).

$^{31}$P NMR (H-decoupled, CDCl$_3$): 25.01 (s).

This structure can be represented by formula:

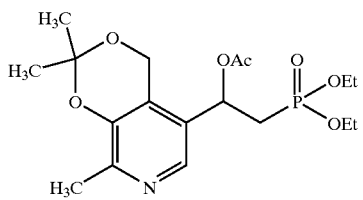

Example 20
Synthesis of diethyl (α⁴,3-O-isopropylidene-3-hydroxy-4-hydroxymethyl-2-methyl-5-pyridyl)-2-hydroxy-1,1-difluoroethylphosphonate To a solution of lithiumdiisopropylamide (LDA) (2.0 M, 1 mL, 2 mmol) in THF (5 mL) was added BuLi (0.5 M, 0.2 mL, 0.1 mmol). The mixture was cooled to −40° C. followed by the addition of diethyl difluoromethyl phosphonate (0.32 mL, 2 mmol) and the reaction mixture stirred at this temperature for 30 minutes. The solution was cooled to −78° C. and (α⁴,3-O-Isopropylidene-3-hydroxy-4-hydroxymethyl-2-methyl-5-pyridyl)methanal (Kortynk et al., J. Org. Chem., 29, 574–579 (1964)) (414 mg, 2 mmol) added in THF (2 mL). The solution was allowed to come to room temperature and stirred overnight. The solvent was evaporated, the residue dissolved in dichloromethane (20 mL), washed with saturated, aqueous NaHCO₃, dried (MgSO₄), and evaporated. Purification by chromatography on silica gel using ethyl acetate:hexane (2:1) gave 528 mg (67%)

$^1$H NMR (CDCl₃, TMS) 1.35 (t, 3H), 1.38 (t, 3H), 1.52 (s, 3H), 1.55 (s, 3H), 2.39 (s,3H), 4.29 (m, 4H), 4.96 (dd, 3H), 8.09 (s, 1H).

$^{19}$F NMR (CDCl₃) −125.99 (ddd), −114.55 (ddd).

$^{31}$P NMR (H-decoupled, CDCl₃): 7.22 (dd).

This structure can be represented by formula:

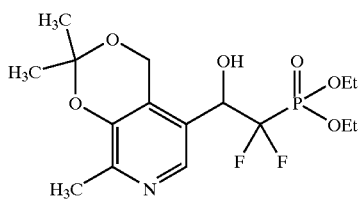

Example 21
Synthesis of diethyl (α⁴,3-O-isopropylidene-3-hydroxy-4-hydroxymethyl-2-methyl-5-pyridyl)-2-oxo-1,1-difluoroethylphosphonate The product of Example 20, of structure XXIV, (420 mg, 1.06 mmol) was dissolved in toluene (50 mL) and MnO₂ (651 mg, 636 mmol) added. The mixture was heated to 50° C. and stirred overnight. The solution was cooled, filtered (Celite) and the solvent evaporated to give the crude product. Purification by chromatography on silica gel ethyl acetate (1:2) gave 201 mg (48%).

$^1$H nmr (CDCl₃, TMS) 1.39 (q, 6H), 1.56 (d, 6H), 2.51 (s,3H), 4.34 (m, 4H), 5.08 (s, 2H), 8.88 (s, 1H).

$^{19}$F NMR (CDCl₃) −109.86 (d).

$^{31}$P NMR (H-decoupled, CDCl₃): 3.96 (t).

This structure can be represented by formula:

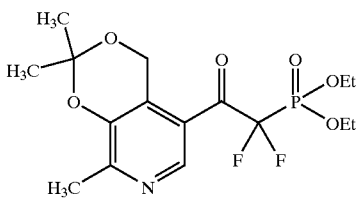

Example 22
Synthesis of diethyl (3-hydroxy-4-hydroxymethyl-2-methyl-5-pyridyl)-2-hydroxy-1,1-difluoroethylphosphonate The product of Example 20, of structure XXIV (489 mg, 1.26 mmol) was dissolved in acetic acid (80% in water, 20 mL) and heated at 80° C. for 6 hours. The solvent was removed by evaporation by codistilling with toluene to remove last traces of acetic acid. The crude product was purified by chromatography on silica gel using dichloromethane:methanol:hexane (5:1:5) as eluent to give 171 mg (38%).

$^1$H NMR (CD₃OD) 1.32 (t, 3H), 1.37 (t, 3H), 2.43 (s,3H), 4.30 (m, 4H), 4.93 (dd, 2H), 5.39 (m, 2H), 8.07 (s, 1H).

$^{19}$F NMR (CD₃OD) −125.55 (dd), −115.77 (dd).

$^{31}$P NMR (H-decoupled, MeOD): 7.82 (dd).

This structure can be represented by formula:

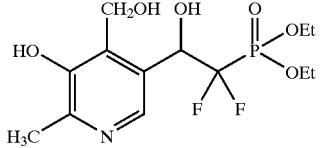

Example 23
Synthesis of diethyl (3-hydroxy-4-hydroxymethyl-2-methyl-5-pyridyl)-2-oxo-1,1-difluoroethylphosphonate The product of Example 21, of structure XXV (198 mg, 0.51 mmol) was dissolved in acetic acid (80% in water, 20 mL) and heated at 80° C. for 6 hours. The solvent was removed by evaporation by codistilling with toluene to remove last traces of acetic acid. The crude product was purified by chromatography on silica gel using dichloromethane:methanol:hexane (5:1:5) as eluent to give 25 mg (14%).

$^1$H NMR (CDCl₃, TMS) 1.38 (m, 6H), 2.37 (s,3H), 4.33 (m, 4H), 4.92 (s, 1H), 7.88 (s, 1H).

$^{19}$F (CDCl₃) −118.32 (d).

$^{31}$P NMR (H-decoupled, CDCl₃): 5.90 (t).

This structure can be represented by formula:

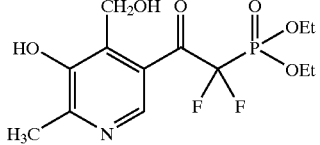

Example 24
Synthesis of diethyl (α⁴,3-O-isopropylidene-2-methyl-3-hydroxy-4-hydroxymethyl-5-pyridylmethyl)malonate To a solution of diethyl malonate (0.76 mL, 798 mg, 4.98 mmol) in tetrahydrofuran (THF) (5 mL) was added LDA (5

M, 1 mL, 5.0 mmol) and stirred at 0° C. for 5 minutes. ($\alpha^4$,3-O-isopropylidene-3-hydroxy-4-hydroxymethyl-2-methyl-5-pyridyl)methylbromide (Imperalli et al, J. Org. Chem., 60, 1891–1894 (1995)) (1.36 g, 5.0 mmol) in THF (5 mL) was added. The reaction was stirred for 2 hours at 0° C. The solvent was evaporated and the residue was dissolved in $Et_2O$. This was washed with water, dried ($MgSO_4$) and evaporated to give the crude product. Purification of the crude mixture by chromatography on silica gel column using diethyl ether:hexane (1:1) gave the malonate derivative 769 mg (44%).

$^1$H NMR ($CDCl_3$, TMS) 1.23 (t, 6H), 1.54 (s, 6H), 2.37 (s, 3H), 3.04 (d, 2H), 3.63 (t, 1H), 4.18 (q, 4H), 4.86 (s, 2H), 7.87 (s, 1H).

Example 25
Synthesis of morpholine pyridoxal-4,5-aminal (1-morpholino-1,3-dihydro-7-hydroxy-6-methylfuro(3,4-c)pyridine)

A mixture of morpholine (20 g) and toluene (100 mL) was stirred and heated using an oil bath set to 100° C. for 15 minutes. Pyridoxal hydrochloride (10 g) was then added and the reaction mixture was stirred at 100° C. for two hours. The reaction mixture was then concentrated by distillation of the toluene and morpholine. The concentrated reaction mixture was washed three times by adding toluene (100 mL) and removing the toluene by distillation. After washing, the residue was dissolved in toluene and filtered, and then hexane was added until precipitation began, at which time the reaction mixture was left overnight at room temperature. Crystals were collected and washed thoroughly with hexane.

Nuclear magnetic resonance spectroscopy (NMR) and mass spectroscopy confirmed the identity of the synthesized compound. The purity of the compound was analyzed by high performance liquid chromatography (HPLC) using a C-18 reverse phase column and water/acetonitrile as solvent (1–100% acetonitrile over 25 minutes).

The product can be represented by the formula:

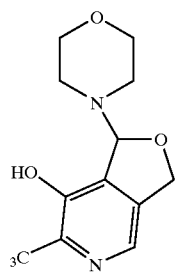

Example 26
Synthesis of the 3-toluate of the morpholine pyridoxal-4,5-aminal(1-morpholino-1,3-dihydro-7-(p-toluoyloxy)-6-methylfuro(3,4-c)pyridine)

Anhydrous powdered potassium carbonate (5 g), acetone (100 mL), and morpholine pyridoxal-4,5-aminal (1-morpholino-1,3-dihydro-7-hydroxy-6-methylfuro(3,4-c)pyridine) (1.11 g, 5 mmoles) were mixed in a nitrogen-cooled, dry flask. The reaction mixture was cooled to between 0 and 5° C. and then p-toluoyl chloride (1.06 g, 6 mmoles) in acetone (20 mL) was added. This mixture was stirred for two hours, followed by filtering out the solid and evaporating the solution to dryness under vacuum. The residue was chromatographed on silica gel using a mixture of ethyl acetate and hexane as solvent.

The purified solid was analyzed by thin layer chromatography (TLC), NMR, and mass spectroscopy. The purity of the synthesized compound was confirmed by HPLC as described in Example 1.

The product can be represented by the formula:

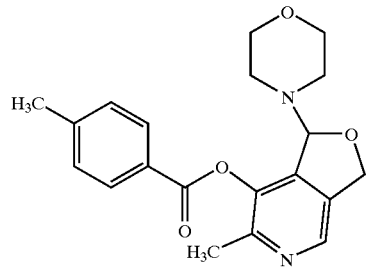

Example 27
Synthesis of the 3-toluate of pyridoxal (2-methyl-3-toluoyloxy-4-formyl-5-hydroxymethylpyridine)

Anhydrous potassium carbonate (10 g), acetone (100 mL), and pyridoxal hydrochloride (2.03 g, 10 mmoles) were mixed in a nitrogen-cooled, dry flask. The mixture was cooled to between 0 and 5° C. and then p-toluoyl chloride (2.12 g, 12 mmoles) in acetone (20 mL) was added. The reaction mixture was stirred for two hours followed by filtering out the solid and evaporating the solution to dryness under vacuum. The residue was chromatographed on silica gel as described in Example 2.

The purified solid was analyzed by TLC, NMR, and mass spectroscopy. The purity of the compound was confirmed by HPLC as described in Example 1.

Alternative to the above-described method, the 3-toluate of pyridoxal is synthesized by reacting the compound of Example 2 with 80% aqueous acetic acid at 60° C. for 30 minutes, and then diluting with water and extracting by ethyl acetate. The ethyl acetate layer is washed with 5% aqueous sodium bicarbonate, dried with magnesium sulfate, and evaporated to dryness. The compound is also analyzed as described supra.

The product can be represented by the formula:

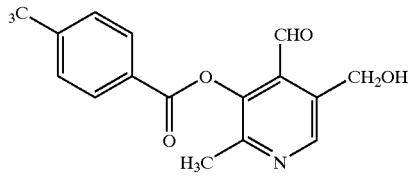

Example 28
Synthesis of 3-β-naphthoate of the morpholine pyridoxal-4,5-aminal(1-morpholino-1,3-dihydro-7-(β-naphthoyloxy)-6-methylfuro(3,4-c)pyridine)

Anhydrous powdered potassium carbonate (5 g), acetone (100 mL), and morpholine pyridoxal-4,5-aminal(1-morpholino-1,3-dihydro-7-hydroxy-6-methylfuro(3,4-c)pyridine) (1.11 g, 5 mmoles) were mixed in a nitrogen-cooled, dry flask. The mixture was cooled to between 0 and 5° C. and then β-naphthoyl chloride (1.06 g, 6 mmoles) in acetone (20 mL) was added. The reaction mixture was stirred for two hours, and then the solid was filtered out and the solution was evaporated to dryness under vacuum. The residue was chromatographed according to Example 2.

The purified solid was analyzed according to Example 2, and the purity was confirmed according to Example 1.

The product can be represented by the formula:

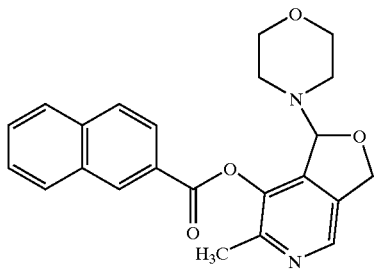

Example 29

Synthesis of the 3-β-naphthoate of pyridoxal(2-methyl-3-9-naphthoyloxy-4- formyl-5-hydroxymethylpyridine Anhydrous potassium carbonate (10 g), acetone (100 mL), and pyridoxal hydrochloride (2.03 g, 10 mmoles) were mixed in a nitrogen-cooled, dry flask. The mixture was cooled to between 0 and 5° C. and then β-naphthoyl chloride (2.12 g, 12 mmoles) in acetone (20 mL) was added and the mixture was stirred for two hours. The solid was filtered out and the solution was evaporated to dryness under vacuum. The residue was chromatographed according to Example 2.

The purified solid was analyzed according to Example 2, and the purity was confirmed according to Example 1.

Alternative to the above-described synthesis, the 3-β-naphthoate of pyridoxal is prepared by reacting the compound of Example 4 with 80% aqueous acetic acid at 60° C. for 30 minutes, followed by diluting with water and extracting by ethyl acetate. The ethyl acetate layer is then washed with 5% aqueous sodium bicarbonate, dried with magnesium sulfate, and evaporated to dryness. The compound is also analyzed as described supra.

The product can be represented by the formula:

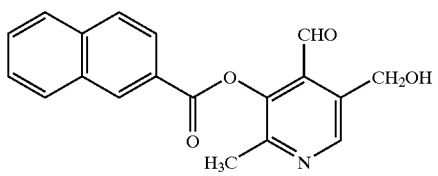

Example 30

Synthesis of 3-pivaloyl of the morpholine pyridoxal-4,5-aminal (1-morpholino-1,3-dihydro-7-pivaloyloxy)-6-methylfuro(3,4-c)pyridine)

Anhydrous powdered potassium carbonate (5 g), acetone (100 mL), and morpholine pyridoxal-4,5-aminal(1-morpholino-1,3-dihydro-7-hydroxy-6-methylfuro(3,4-c) pyridine) (1.11 g, 5 mmoles) were mixed in a nitrogen-cooled, dry flask. The mixture was cooled to between 0 and 5° C. and then pivaloyl chloride (trimethylacetyl chloride) (720 mg, 6 mmoles) in acetone (20 mL) was added. The reaction mixture was stirred for two hours. The solid was then filtered out and the solution was evaporated to dryness under vacuum. The residue was chromatographed according to Example 2.

The purified solid was analyzed according to Example 2, and the purity was confirmed according to Example 1.

The product can be represented by the formula:

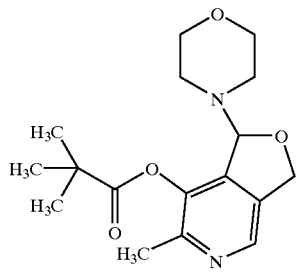

Example 31

Synthesis of 3-dimethylcarbamoyl of the morpholine pyridoxal-4,5-aminal (1-morpholino-1,3-dihydro-7-(dimethylcarbamoyloxy)-6-methylfuro(3,4-c)pyridine)

Anhydrous powdered potassium carbonate (5 g), acetone (100 mL), and morpholine pyridoxal-4,5-aminal(1-morpholino-1,3-dihydro-7-hydroxy-6-methylfuro(3,4-c) pyridine) (1.11 g, 5 mmoles) were mixed in a nitrogen-cooled, dry flask. The mixture was cooled to between 0 and 5° C. and then dimethylcarbamoyl chloride (642 mg, 6 mmoles) in acetone (20 mL) was added. The reaction mixture was stirred for two hours. The solid was then filtered out and the solution was evaporated to dryness under vacuum. The residue was chromatographed according to Example 2.

The purified solid was analyzed according to Example 2, and the purity was confirmed according to Example 1.

The product can be represented by the formula:

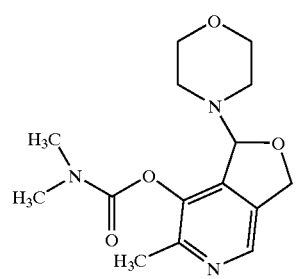

Example 32

Synthesis of 3-acetylsalicyloyl of the morpholine pyridoxal-4,5-aminal (1-morpholino-1,3-dihydro-7-acetylsalicyloxy)-6-methylfuro(3,4-c)pyridine)

Anhydrous powdered potassium carbonate (5 g), acetone (100 mL), and morpholine pyridoxal-4,5-aminal(1-morpholino-1,3-dihydro-7-hydroxy-6-methylfuro(3,4-c) pyridine) (1.11 g, 5 mmoles) were mixed in a nitrogen-cooled, dry flask. The mixture was cooled to between 0 and 5° C. and then acetylsalicyloyl chloride (1.09 g, 6 mmoles) in acetone (20 mL) was added. The reaction mixture was stirred for two hours. The solid was then filtered out and the solution was evaporated to dryness under vacuum. The residue was chromatographed according to Example 2.

The purified solid was analyzed according to Example 2, and the purity was confirmed according to Example 1.

The product can be represented by the formula:

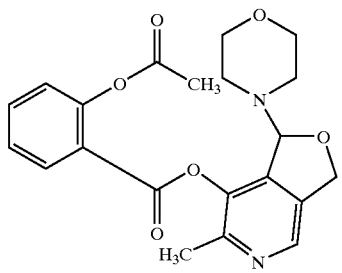

Example 33
Bioavailability of Pyridoxal-5'-Phosphate and Pyridoxal after the Administration of a Compound of the Invention The bioavailability of pyridoxal-5'-phosphate and pyridoxal after the administration of a compound of the invention was determined by measuring pyridoxal-5'-phosphate and pyridoxal levels in blood plasma after administering a compound of the invention to rats.

The rats studied were twelve male Sprague-Dawley rats (Charles River, Montreal, Canada) chosen at random. These rats were divided into four groups. The first group was administered pyridoxal-5'-phosphate (Sigma, Milwaukee, Wis.) as a control; the second group was administered 3-pivaloylaminal (synthesized according to Example 6); the third group was administered 3-dimethylcarbamoylaminal (synthesized according to Example 7); and the fourth group was administered 3-acetylsalicoylaminal (synthesized according to Example 8).

Approximately 24 to 48 hours prior to administering pyridoxal-5'-phosphate or a compound of the invention to the rats, an initial blood sample (500–600 µL) was obtained from each rat. The blood samples were collected from the orbital sinus of each rat according to standard methods. The blood samples were placed into EDTA-Microtainer Brand Tubes (Becton Dickinson) and the plasma was separated from blood by centrifugation. The plasma samples were stored at −80° C. After withdrawal of the blood sample, each rat was then intravenously injected with saline in an amount equivalent to the blood withdrawn.

Each rat fasted for eight hours prior to administering pyridoxal-5'-phosphate or a compound of the invention. Each rat then received by oral gavage pyridoxal-5'-phosphate or a compound of the invention (10 mg/kg of body weight) according to the group with which the rat was identified.

Blood samples were then collected from each rat as described above and stored as described above. Blood samples were collected at about 15, 30, 60, 180, 360, 720, 1440, and 2160 minutes after administration of pyridoxal-5'-phosphate or the compound of the invention.

After all samples were collected, the frozen plasma samples were thawed at about room temperature, and the pyridoxal-5'-phosphate and pyridoxal levels were determined for each sample. To determine the pyridoxal-5'-phosphate and pyridoxal levels, the protein was first precipitated from the plasma. Each sample of protein-free plasma was then combined with perchloric acid and phosphate buffer. Each sample was then evaluated by high performance liquid chromotography on a C-18 reverse-phase silica-gel column. Each sample was detected with excitation at 300 mm and emission at 400 mm. The amounts of pyridoxal-5'-phosphate and pyridoxal were quantified using standard curve and integration of the peaks. The results are shown in FIGS. 1–4.

The results show that 3-pivaloylaminal (FIG. 2), 3-dimethylcarbamoylaminal (FIG. 3), and 3-acetylsalicoylaminal (FIG. 4) provided pyridoxal and pyridoxal-5'-phosphate levels comparable to the levels provided by administering pyridoxal-5'-phosphate (FIG. 1).

Example 34
Rat Model of Cerebral Ischemia

Male Wistar rats (250–300 g) were housed in the animal facility for a period of 12 days and given food and water ab libitum. Animals were randomly assigned to groups (n=8/group) of a) control group b) post-ischemia PLP treatment 10 mg/kg c) post-ischemia PLP treatment 20 kg/mg and d) post-ischemia PLP treatment 40 mg/kg.

The rats of each group were anaesthetized to surgical depth initially with 3% halothane, and maintained with 1.5% halothane in a 70% $N_2O$/30% $O_2$ (vol./vol.) mixture. Animal core temperature was maintained at approx 37° C. using a heating pad and an overhead lamp. Temperature was measured with a rectal thermometer.

A midline longitudinal incision of approx 2.0 cm was made in the cervical area. Both common carotid arteries (CCA) were dissected from the surrounding tissue and both the right internal carotid artery (ICA) and the right external carotid artery (ECA) were exposed to a maximal length. Branches of the right ECA will be occluded with electro-coagulation and the distal portion ligated. The right CCA and ICA were occluded by temporary clamping, after which the distal end of the ECA was cut to allow catheter insertion. A loose 5.0 silk suture was tied around the proximal right ECA. A PE-50 catheter [Becton-Dickinson, N.J., USA] (0.3 mm O.D at the tip of the catheter and O.D. 0.97 in the catheter body) was attached to a 1 mm syringe filled with 0.5 ml bovine alpha-thrombin (Thrombostat, Parke-Davis).

The catheter was introduced into the ICA from the ECA and CCA via a small puncture and the silk suture tied around the ECA to prevent bleeding and dislodgement. This was followed by the removal of vascular clips from the ICA and CCA. 10 ul of blood was withdrawn into the catheter and kept in place for 15 minutes for formation of a thrombin clot. Subsequently 17 mm of the catheter (calculated from the puncture site) was gently advanced through the ECA and extra-cranial portion of the ICA to approximately 2 mm from the origin of the middle cerebral artery. After temporary occlusion of the CCAs bilaterally to slow blood flow, the clot was introduced into the ICA. The clip of the contralateral CCA was removed five minutes later and the catheter was removed 10 minutes after the clot introduction. The ipsilateral ICA was then ligated prior to the removal of the clip on the right CCA, 15 minutes after clot injection. The incision was then sutured and the animals allowed to recover from anesthesia whereupon they were given free access to food & water.

1. Neurological Deficit Evaluation

Neurological deficit evaluation was conducted at 2 and 24 hours after injection of thrombus. The neurological findings were scored on a four-point grade scale: no observable deficit—0; forelimb flexion—1; forelimb flexion and decreased resistance to lateral push—2; forelimb flexion, decreased lateral push resistance and unilateral circling in three successive trials—3. A score of 4 was given to animals with a score of 3 plus decreased consciousness. The animals were observed for any other neurological abnormalities not included in the grade-scale.

2. Measurement of Infarct Damage

The infarcted brain tissue in the right MCA territory was differentiated using the 2,3,5-triphenyltetrazolium chloride (TTC) staining method. The rats were perfused transcardially with 120 ml 0.9% normal saline under deep anaesthesia, 24 hours after ischemia. The brain was then removed and cooled in ice-cold saline for 5 minutes after which it was dissected in the coronal plane at 2 mm intervals using a rat brain matrix and stored in 10% buffered formalin for fixing. The stained sections were colour scanned within seven days. The 2 mm thick coronal sections were placed directly on the scanning screen and scanned from rostral to caudal ends, with attention paid to soaking up formalin to prevent shadows, and the use of a black background.

Image contrast and brightness was adjusted with Photoshop 4.0; measurements were made by manually outlining the margins of infarct areas in each section. The total volume of infarction was determined by integrating the distance values of the eight chosen sections. Values were corrected for any brain edema.

3. Therapeutic Regimen:

Control animals were given 3 mL saline (iv) at 2 hours following cerebral ischemia. The pre-ischemia treatment group was given PLP (10 mg/kg, iv in 3 mL) over 30 minutes 1 hour prior to ischemic insult. The post-ischemia groups received PLP at 5, 10, or 20 mg/kg iv at 2 hours following cerebral ischemia.

4. Statistical Analysis:

All data was expressed as mean±SD. Two-tailed paired Students t-tests were used to compare differences between values obtained before and after treatment. Statistical analysis of more than two groups of animals were performed with ANOVA, with subsequent individual comparisons by Scheffe's test. Differences were considered significant at p>0.05. The results of the effect of PLP on infact volume reduction are shown in Table 1.

TABLE 1

|  | Infarct Volume (mean) | Infarct Volume (standard deviation) |
| --- | --- | --- |
| Control group | 37.74%, | 11.3 |
| 10 mg/kg treatment group: | 28.25%, | 9.30 |
| 20 mg/kg treatment group | 27.4%, | 13.1 |
| 40 mg/kg treatment group: | 19.3%, | 11.02 |

5. Neurobehavioral Scores

Score decreased from 3.6 to 3 in the 10 mg/kg group, from 3.8 to 3 in the 20 mg/kg group, and from 3.8 to 1.9 (p<0.001) in the 40 mg/kg group. There was no difference in the number of seizures in any of the three groups. The risk of hemorrhage did not increase with higher doses. There was a trend towards decreased mortality (2 in control group, 3 in 10 mg/kg group, 1 in 20 mg/kg group, 0 in 40 mg/kg group).

As shown in the above example, infarct reduction was statistically significant at 40 mg/kg dose. Furthermore, there was a dose-dependant therapeutic effect of PLP on infarct size and neurobehavioral activity.

Pyridoxal-5-phosphate in the rat model of ischemia and reperfusion injury demonstrates anti-ischemic effects and benefits against ischemia reperfusion injury. Thus, treatment with pyridoxal-5-phosphate, compounds capable of increasing the levels of pyridoxal-5-phosphate in vivo, or compounds capable of mimicing the biological activity of pyridoxal-5-phosphate are beneficial against the pathology of cerebral stroke.

Although embodiments of the invention have been described above, it is not limited thereto, and it will be apparent to persons skilled in the art that numerous modifications and variations form part of the present invention insofar as they do not depart from the spirit, nature and scope of the claimed and described invention.

We claim:

1. A method of treating cerebral ischemia or ischemic stroke in a mammal comprising administering a therapeutically effective amount of at least one compound of the formula

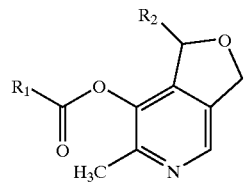

wherein $R_1$ is alkyl or alkenyl, in which alkyl or alkenyl can be interrupted by nitrogen, oxygen, or sulfur, and is optionally substituted at the terminal carbon by hydroxy, alkoxy, alkanoyloxy, alkanoyloxyaryl, alkoxyalkanoyl, alkoxycarbonyl, or dialkylcarbamoyloxy;

alkoxy;

dialkylamino;

alkanoyloxy;

alkanoyloxyaryl;

alkoxyalkanoyl;

alkoxycarbonyl;

dialkylcarbamoyloxy;

aryl, aryloxy, arylthio, or aralkyl, in which aryl can be substituted by alkyl, alkoxy, amino, hydroxy, halo, nitro, or alkanoyloxy; and $R_2$ is a secondary amino group; or a pharmaceutically acceptable salt thereof.

2. The method of claim 1, wherein said $R_1$ is phenyl or naphthyl in which phenyl or naphthyl is unsubstituted or substituted by one or more groups of $C_{1-4}$ alkyl, $C_{1-4}$ alkoxy, amino, hydroxy, halo, nitro, or $C_{1-4}$ alkanoyloxy.

3. The method of claim 1, wherein said $R_1$ is (2-acetoxy-2-methyl)propanyl, dimethylamino, or 1-ethanoyloxy-1-methylethyl.

4. The method of claim 1, wherein said wherein $R_1$ is tert-butyl.

5. The method of claim 1, wherein said wherein $R_1$ is methoxy or ethoxy.

6. The method of claim 1, wherein said $R_1$ is toluyl, naphthyl, phenyl, or 1-ethanoyloxyphenyl.

7. The method of claim 1, wherein said $R_1$ is dimethylamino, acetylsalicyl, or 2,2-dimethylethyl.

8. The method of claim 1, wherein said $R_2$ is a group of the formula

wherein $R_3$ and $R_4$ are each independently alkyl or when taken together form a ring with the nitrogen atom and which ring may optionally be interrupted by a nitrogen or oxygen atom.

9. The method of claim 1, wherein said $R_2$ is piperidino.

10. The method of claim 1, wherein said $R_2$ is morpholino or piperazino.

11. The method of claim 1, wherein said compound is 1-morpholino-1,3-dihydro-7-(p-toluoyloxy)-6-methylfuro(3,4-c)pyridine.

12. The method of claim 1, wherein said compound is 1-morpholino-1,3-dihydro-7-(β-naphthoyloxy)-6-methylfuro(3,4-c)pyridine.

13. The method of claim 1, wherein said compound is 1-morpholino-1,3-dihydro-7-pivaloyloxy-6-methylfuro(3,4-c)pyridine.

14. The method of claim 1, wherein said compound is 1-morpholino-1,3-dihydro-7-(dimethylcarbamoyloxy-6-methylfuro(3,4-c)pyridine.

15. The method of claim 1, wherein said compound is 1-morpholino-1,3-dihydro-7-acetylsalicyloxy-6-methylfuro (3,4-c)pyridine.

16. The method of claim 1, wherein said therapeutically effective amount is in a range of about 0.5–100 mg/kg per day of the mammal's body weight.

17. The method of claim 1, wherein said compound is administered enterally or parenterally.

* * * * *